United States Patent
Geddes et al.

(10) Patent No.: US 9,244,012 B2
(45) Date of Patent: Jan. 26, 2016

(54) ENHANCED LUMINESCENCE FROM NANOPOLISHED SURFACES AND PLATE WELLS

(71) Applicants: Chris D. Geddes, Bel-Air, MD (US); Anatoliy I. Dragan, Towson, MD (US)

(72) Inventors: Chris D. Geddes, Bel-Air, MD (US); Anatoliy I. Dragan, Towson, MD (US)

(73) Assignee: UNIVERSITY OF MARYLAND, BALTIMORE COUNTY, Baltimore, MD (US)

( * ) Notice: Subject to any disclaimer, the term of this patent is extended or adjusted under 35 U.S.C. 154(b) by 561 days.

(21) Appl. No.: 13/627,387

(22) Filed: Sep. 26, 2012

(65) Prior Publication Data
US 2013/0156938 A1    Jun. 20, 2013

Related U.S. Application Data

(60) Provisional application No. 61/539,146, filed on Sep. 26, 2011.

(51) Int. Cl.
*G01N 21/64* (2006.01)
*C09D 5/22* (2006.01)
*B05D 1/06* (2006.01)

(52) U.S. Cl.
CPC *G01N 21/64* (2013.01); *B05D 1/06* (2013.01); *C09D 5/22* (2013.01); *G01N 21/648* (2013.01); *Y10T 428/12028* (2015.01)

(58) Field of Classification Search
None
See application file for complete search history.

(56) References Cited

U.S. PATENT DOCUMENTS

| | | |
|---|---|---|
| 7,095,502 B2 | 8/2006 | Lakowicz et al. |
| 7,400,397 B2 | 7/2008 | Lakowicz et al. |
| 7,718,804 B2 | 5/2010 | Geddes et al. |
| 7,732,215 B2 | 6/2010 | Geddes et al. |
| 7,776,528 B2 | 8/2010 | Lakowicz |
| 7,939,333 B2 | 5/2011 | Geddes et al. |
| 7,989,220 B2 | 8/2011 | Lakowicz et al. |
| 8,008,067 B2 | 8/2011 | Geddes et al. |
| 8,027,039 B2 | 9/2011 | Lakowicz et al. |
| 8,034,633 B2 | 10/2011 | Geddes |
| 8,075,956 B2 | 12/2011 | Geddes et al. |
| 8,101,424 B2 | 1/2012 | Geddes |
| 8,114,598 B2 | 2/2012 | Geddes et al. |
| 8,182,878 B2 | 5/2012 | Geddes et al. |
| 8,318,087 B2 | 11/2012 | Geddes |
| 8,338,602 B2 | 12/2012 | Geddes et al. |
| 8,404,450 B2 | 3/2013 | Geddes et al. |
| 8,569,502 B2 | 10/2013 | Geddes et al. |
| 8,618,505 B2 | 12/2013 | Geddes |
| 8,679,402 B2 | 3/2014 | Geddes |

(Continued)

OTHER PUBLICATIONS

Aslan, K. et al. (2005) Annealed Silver-Island Films for Applications in Metal-Enhanced Fluorescence: Interpretation in Terms of Radiating Plasmons. Journal of Fluorescence 15, 643-654.

(Continued)

*Primary Examiner* — Shamim Ahmed
*Assistant Examiner* — Bradford Gates
(74) *Attorney, Agent, or Firm* — Marianne Fuierer; Moore & Van Allen, PLLC

(57) ABSTRACT

The present invention relates to a method for fabricating a new silver coating/nanoparticle scaffold that significantly enhances the luminescence of near-field fluorophores via the metal enhanced fluorescence phenomenon. The silver coating/nanoparticle scaffold can be used for numerous applications in metal-enhanced fluorescence.

18 Claims, 33 Drawing Sheets

(56) References Cited

U.S. PATENT DOCUMENTS

| | | | |
|---|---|---|---|
| 8,679,855 | B2 | 3/2014 | Geddes |
| 8,722,428 | B2 | 5/2014 | Geddes |
| 8,735,175 | B2 | 5/2014 | Geddes |
| 8,759,110 | B2 | 6/2014 | Geddes |
| 2003/0228682 | A1 | 12/2003 | Lakowicz |
| 2006/0256331 | A1 | 11/2006 | Geddes |
| 2007/0207335 | A1* | 9/2007 | Karandikar et al. ........... 428/560 |
| 2007/0269826 | A1 | 11/2007 | Geddes |
| 2008/0215122 | A1 | 9/2008 | Geddes |
| 2009/0022766 | A1 | 1/2009 | Geddes |
| 2009/0325199 | A1 | 12/2009 | Geddes |
| 2011/0020946 | A1 | 1/2011 | Geddes |
| 2011/0136154 | A1* | 6/2011 | Geddes ......................... 435/7.92 |
| 2011/0207236 | A1 | 8/2011 | Geddes |
| 2012/0021443 | A1 | 1/2012 | Geddes |
| 2013/0020503 | A1* | 1/2013 | Geddes ........................ 250/459.1 |

OTHER PUBLICATIONS

Aslan, K. et al. (2005) Angular-Ratiometric Plasmon-Resonance Based Light Scattering for Bioaffinity Sensing. J. Am. Chem. Soc. 127, 12115-12121.

Aslan, K. et al. Gryczynski, et al. (2005) Metal-Enhanced fluorescence: an emerging tool in biotechnology. Current Opinion in Biotechnology 16, 55-62.

Aslan, K et al. (2006) Metal-Enhanced Fluorescence-Based RNA Sensing. J. Am. Chem. Soc. 128, 4206-4207.

Aslan, K. et al. (2006) Metal-Enhanced fluorescence from silver nanoparticle-deposited polycarbonate substrates. Journal of Materials Chemistry 16, 2846-2852.

Aslan, K. et al. (2007) Metal-Enhanced Fluorescence (MEF): Progress towards a Unified Plasmon-Flurophore Theory. Biophysical Journal, 371A-371A.

Aslan, K. et al. (2007) Angular-dependent metal-enhanced fluorescence from silver-colloid-deposited films: opportunity for angular-ratiometric surface assays. Analyst 132, 1112-1121.

Chowdhury, M.H. et al. (2006) Metal-Enhanced chemiluminescence: Radiating plamons generated from chemically induced electronic excited states. Applied Physics Letters 88, 173104.

Chowdhury, M.H. (2006) Multicolor Directional Surface Plasmon-Coupled Chemiluminescence. Journal of Physical Chemistry B 110, 22644-22651.

dos Santos, David S. et al. (2007) Selective surface-enhanced fluorescence and dye aggregation with layer-by-layer film substrates. Analyst 132, 450-454.

Feofanov, A. et al. (1997) Nondisturbing and Stable SERS-Active Substrates with Increased Contribution of Long-Range Component of Raman Enhancement Created by High-Temperature Annealing of Thick Metal Films. Analytical Chemistry 69, 3731-3740.

Geddes, C.D. et al. (2002) Metal-Enhanced Fluorescence. Journal of Fluorescence 12, 121-129.

Geddes, C.D. (2003) Electrochemical and Laser Deposition of Silver for Use in Metal-Enhanced Fluorescence. Langmuir 19, 6236-6241.

Lakowicz, J.R. (2001) Radiative Decay Engineering: Biophysical and Biomedical Applications. Analytical Biochemistry 298, 1-24.

Previte, M.J.R. et al. (2007) Metal-Enhanced Surface Plasmon-Coupled Phosphoresnce. J. Phys. Chem. 111, 6051-6059.

Retnakumari, A. et al. (2010) Molecular-receptor-specific, non-toxic, near-infrared-emiting Au cluster-protein nanoconjugates for targeted cancer imagining. Nanotechnology, 21 (055103) 1-12.

Richards, C.I. (2008) Oligonucleotide-Stabilized Ag Nanocluster Fluorophores. J. Am. Chem. Soc. 130 5038-5039.

Strehle, K.R. (2007) A Resproducible Surface-Enhanced Raman Spectroscopy Approach, Online SERS Measurements in a Segmented Microfluidic System. Anal Chem 79, 1542-1547.

Yguerabide, J. et al. (1998) Light-Scattering Submicroscopic Particles as Highly Fluorescent Analogs and Their Use as Tracer Labels in Clinical and Biological Applications. Analytical Biochemistry 262, 137-156.

Yu, Q. et al. (2007) Probing the Protein Orientation on Charged Self-Assembled Monolayers on Gold Nanohole Arrays by SERS. Langmuir 23, 8659-62.

Zhang, Y. et al. (2006) Metal-Enhanced phosphorescence. Chemical Physics Letters 432, 528-532.

Zhang, C. et al. (2007) Surface enhanced Raman with anodized aluminum oxide films. J. Chem. Phys. 127, 044701.

Zhang, Y. et al. (2007) Metal-Enhanced fluorescence: Surface plamons can radiate a fluorophore's structured emission. Applied Physical Letters, 90, 053107-1-053107-3.

Zhang, Y. et al. (2007) Metal-Enhanced fluorescence from copper substrates. Applied Physics Letters 90, 053107.

* cited by examiner

ENHANCED LUMINESCENCE FROM NANOPOLISHED SURFACES AND PLATE WELLS

CROSS-REFERENCES TO RELATED APPLICATION

The present application claims priority to U.S. Provisional Patent Application No. 61/539,146 filed on Sep. 26, 2011 the contents of which are hereby incorporated by reference herein for all purposes.

BACKGROUND OF THE INVENTION

1. Field of the Invention

The present invention relates to metallized substrate, and more particularly, to a multiplicity of layers wherein each layer comprises a multiplicity of metallic nanoparticles having substantially the same size to provide surfaces that exhibit metal enhanced luminescence.

2. Related Art

In recent years it has been described and demonstrated that there are many new favourable photophysical effects of electronically excited states (fluorophores/luminophores) in close-proximity to plasmon resonant particles.(1-4) The coupled fluorophore lifetime is also observed to be much shorter than the "free-space lifetime," reflecting the very fast "plasmon" lifetime of the coupled quanta. (5-7) Further, it is thought that the metal-enhanced fluorescence (MEF) effect is a consequence of an excited state coupling with the scattering mode of nanoparticles, which is thought to account for very fast MEF lifetimes, i.e. a coupled elastic scattering event.(3,8) For metallic nanoparticles, the extinction spectrum is comprised of both an absorption and scattering component.(9) For smaller particles (<25 nm), then the extinction is for the most part dominated by absorption, while for larger particles, by scattering.

While the mechanism for MEF is fairly new,(3) compelling data has been reported wherein: i) MEF is seen to be more pronounced for larger particles; ii) the wavelength dependence of MEF suggests a correlation between the scattering spectra of the nanoparticles and the emission spectra of the fluorophores; iii) MEF is angular dependent,(10) both from an observation and excitation perspective, similar to scattering by nanoparticles themselves(11); iv) metals ideal for MEF are those with high free electron densities(12) and v) metallic material has been shown to couple fluorophore emission, when fluorophores are positioned less than 100 nm from the surface. In addition, the coupled emission has been shown to be completely p-polarized, strongly indicating that the coupled-plasmon system is radiating.(13,14)

Silver is usually the noble metal of choice (12,15-17) for applications in MEF and Surface-Enhanced Raman Spectroscopy. The preparation of silvered substrates include several modes of deposition, such as by wet chemistry,(18) a layer-by-layer deposition technique,(19) electrochemically,(20) on glass,(21) and plastic substrates. (22) One of the most commonly used techniques is vapor-deposition as it yields the most reproducible substrates amongst the deposition techniques aforementioned.

However, heretofore producing silver substrates for providing the MEF effect has included a single layer of particles deposited directly on the substrate. Although the results have been found to be very satisfactory, it would be advantageous to provide a substrate with multiple layers of such nanoparticles thereby providing further enhancement of the signal and methods of forming same.

SUMMARY OF THE INVENTION

The present invention relates to a substrate comprising a multiplicity of discrete metallic layers, wherein each layer comprises discrete metallic nanoparticles, having substantially the same size, to provide a substrate with enhanced luminescence.

The present invention relates to a method of fabricating a metallized substrate that includes multiple layers of metallic nanoparticles that exhibit increased metal enhanced fluorescence, the method comprising:
a) providing substrate;
b) providing a metal containing solution, wherein the metal has plasmonic activity, contacting the metal containing solution with the substrate and heating same to a temperature of from about 30° C. to about 50° C. for a deposition time period ranging from 1 minute to 7 minutes to provide for deposition of metallic nanoparticles;
c) transferring the heated substrate to a freezing chamber for a time period ranging from about 1 minute to 4 minutes to form a chilled substrate;
d) transferring the chilled substrate back to a heating environment for a time period being the same as step b) or shorter than the previous heating period;
e) removing the solution; and
f) repeating steps b) and c) for at least one more time and more preferably from 4 to 19 times to provide a multiplicity of layers of metallic nanoparticles, wherein the nanoparticles are distinct and substantially the same size.

Preferably, for a 100 ml beaker, a metal containing solution includes $AgNO_3$ with a concentration of about 1% to about 5% in an amount from about 10 ml to about 30 ml. Additionally, NaOH is added to the solution wherein the concentration of NaOH is from about 5% to about 20% concentration in an amount from about 50 ul to about 100 ul wherein the solution becomes turbid. Also included in the solution is an amount of $NH_4OH$, with a concentration of about 20% to 40% and in an amount from about 300 ul to about 700 ul. Importantly, glucose is added to the solution in an amount from about 2 ml to about 7 ml to provide from about 4.5% to 15% w/v of glucose.

Notably, the amounts described above can be increased proportionally depending on the size of the initial amount of solution required. The prepared solution is introduced into the substrate container, such as high-throughput screening wells, and the particle formation begins. Initially the container substrate with the solution is heated for a specific length of time ranging from about 1 minute to about 7 minutes, wherein the heating time determines the size of the particles. For example the heating time frame can be two minutes to provide a nanoparticle having a diameter of about 100 nm, and wherein heating for 7 minutes provides for a spherical diameter of about 350 nm. The heating temperature is preferably between 40° C. and 60° C. The range of particles sizes can range from about 50 nm for 1 minute of heating/deposition time and up to about 350 nm for a 7 minute heating/deposition time.

After the heating process, the substrate is moved to a freezing chamber wherein the temperature is about 0° C. and cooled for approximately the same time as that of the heating. For the first layer, the substrate is reheated to for approximately the same time and temperature. For each subsequent layer, the heating time is the same as the previous heating time or increased about one (1) minute. After the heating time period is completed, the substrate is introduced into the freezing chamber and then the heating and freezing procedures are repeated. The number layers can be from 2 layers to 20 and more preferably from about 5 layers to 20 layers. Notably, the emission signal for excited fluorophores increases continuously as the number of layers increase to reach a limit level after about 12 layers.

The substrate may be a container type vessel having at least a bottom point and sides attached to the bottom point for holding the metal containing solution during the deposition process. In the alternative, a plate substrate can be introduced into a container that holds the metal containing solution for deposition of metallic particles on the plate. The plate is then treated as above.

The metallic nanoparticles may be fabricated from any metallic material that provides for plasmonic emissions and Silver, Gold, Aluminium, Zinc, Rhodium, Copper, Nickel, Palladium, Indium, Tin, Iron, Tungsten, Platinum, Germanium and a combination thereof.

The surface substrate container can be fabricated from glass, quartz, metallic oxide containing or a polymeric material. Preferably, the nanoparticles have an approximate cross-sectional diameter from about 50 nm to about 350 nm.

In yet another aspect, the present invention relates to a detection method exhibiting increased fluorescence emitted during metal-enhanced fluorescence sensing, the detection method comprising:

i) providing a metallized surface container with a multiplicities of layers of metallic nanoparticles, the metallized surface container fabricated by the following method,
   a) providing a plasma cleaned substrate type container having at least a bottom point and sides attached to the bottom point;
   b) providing a silver containing solution and pouring into the plasma cleaned substrate container and heating same to a temperature of from about 30° C. to about 50° C. for a time period ranging from 1 minute to 4 minutes to form a heated substrate;
   c) transferring the heated substrate to a freezing chamber for a time period range from about 1 minute to 4 minutes to form a cold substrate;
   d) transferring the cold substrate back to a heating environment for a time being the same as step b) or shorter than the previous heating period;
   e) removing the solution; and
   f) repeating steps b) and c) from at least one more time, and more preferably from about 4 to 19 times to provide a multiplicity of layers of silver nanoparticles, wherein the nanoparticles are distinct and substantially the same size;
ii) providing a an intrinsic or extrinsic fluorophore for disposing near the near the surface of the top layer of nanoparticles;
iii) exciting the fluorophore with an electromagnetic source to cause fluorescing; and
iv) measuring the emissions from the system.

The detection method can be further enhanced by applying electromagnetic energy in the microwave range to cause an increase in heat in the system thereby increasing the kinetics of any chemical reactions occurring within the detection system The substrate comprising multiple layers of metallic nanoparticles can be used for fluorescence, phosphorescence and chemiluminescence signatures and a range of organic and inorganic chromophores, including quantum dots, GFP, semi-conductor emitters and silica nanoparticles. The substrate comprising multiple layers of metallic nanoparticles provides for significantly enhanced intensity of fluorescence, decreased lifetime and increased luminophore photostability. The metallic nanoparticles may be fabricated from any metallic material that provides for plasmonic emissions and Silver, Gold, Aluminium, Zinc, Rhodium, Copper, Nickel, Palladium, Indium, Tin, Iron, Tungsten, Platinum, Germanium and a combination thereof.

The substrate comprising multiple layers of metallic nanoparticles can be used to develop surfaces spanning broad wavelength ranges and can be used to change the reflective and/or absorption properties of metalized substrates, yet still provide for enhanced luminescence signatures.

In one aspect the present invention provides a substrate comprising non-connecting metalized nanoparticles that are spatially separated, wherein the metalized structures comprise layers with a dielectric material, such as a metal oxide layer positioned therebetween. Further, the structures may include one layer of a single metal, an oxide layer and another metal layer of the same or a different metal wherein the oxide layer is positioned between the metal layers.

In one aspect, the present invention provides for a detection system, the system comprising:
a) a substrate comprising multiple layers of metallic nanoparticles according to present invention;
b) at least one excitable molecule that is positioned near the top surface of the multiple layers in a range from about 5 nm to 50 nm, wherein the excitable molecule is selected from the group of an intrinsic fluorophore, extrinsic fluorophore, fluorescent dye, and luminophores;
c) a source of electromagnetic energy for providing excitation energy to excite the molecule; and
d) a detector for detecting emissions from the excited molecule and/or the surface of metallic nanoparticles on the exposed layers.

The emission enhancement may be observed when the fluorophores or luminophores are positioned from about 5 nm to about 200 nm from the metal surfaces. Preferable distances are about 5 nm to about 30 nm, and more preferably, 5 nm to about 20 nm from the metal surfaces.

Another aspect of the invention relates to a method of enhancing emissions from fluorescence, chemiluminescence, bioluminescence, and luminescence molecules and reactions that exhibit emissions in wavelengths from UV-visible to near IR.

The present invention relates to a method of detection using plasmonic emissions from metallic surfaces caused by fluorescence, chemiluminescence or bioluminescence based reactions. These plasmonic emissions emitted from metallic surface plasmons are generated either with an external excitation of an adjacent luminophore or without such external excitation due to chemically induced electronically excited states.

In yet another aspect, the present invention relates to a method of metal-enhanced fluorescence sensing, comprising:
a) applying multiple layers of metallic nanoparticles to a surface used in a detection system;
b) introducing a solution containing at least one biomolecule for disposing near the metallic nanoparticles positioned on the top surface of the multiple layers, wherein the biomolecule is capable of a chemically induced electronically excited state;
c) triggering the chemically induced electronically excited state of the biomolecule; and
d) measuring the bioluminescent or chemiluminescent intensity.

In yet another aspect, the present invention relates to a method for detecting a target molecule in a sample, the method comprising:

a) providing a system comprising:
   i) a substrate comprising multiple layers of metallic nanoparticles, wherein the metallic nanoparticles positioned on the top surface of the multiple layers have attached thereto a capture biomolecular probe with an affinity for the target molecule; and
   ii) a free biomolecular probe with an affinity for the target molecule, wherein the free biomolecular probe has attached thereto a fluorophore;
b) contacting the sample suspected of including the target molecule with the metallic nanoparticles and capture biomolecular probes, wherein any available target molecules binds to the capture biomolecular probes; and
c) contacting the bound target molecule with the free biomolecular probe, wherein binding of the free biomolecular probe to the target molecule causes the fluorophore to be positioned a sufficient distance from the metallic nanoparticles to enhance fluorescence emission when excited by an irradiating source.

The substrate positioned beneath the multiple layers of metallic nanoparticles may include glass, quartz, plastics (such as on the bottom of HTS plates, polystyrene, polycarbonate), semiconductors, paper, cellulose, cotton, nylon, silk, very thin metal sheets, sapphire, diamond, ruby and dielectric materials.

An oxide layer may be positioned between two layers of the nanoparticles. The oxide layer coating may include at least one metal selected from the group consisting of Al, Ti, Fe, Cu, Zn, Y, Zr, Nb, Mo, In, Si, Sn, Sb, Ta, W, Pb, Bi and Ce and having a valence of from 2 to 6. The form of the oxide of such a metal may, for example, be $Al_2O_3$, $SiO_2$, $TiO_2$, $Fe_2O_3$, $CuO$, $ZnO$, $Y_2O_3$, $ZrO_2$, $Nb_2O_5$, $MoO_3$, $In_2O_3$, $SnO_2$, $Sb_2O_5$, $Ta_2O_5$, $WO_3$, $PbO$ or $Bi_2O_3$. These metal oxides may be used alone or in combination with other types of coatings. Preferably, the oxide is a silicon oxide, more preferably, $SiO_2$. The vapor deposition of $SiO_2$ is a well-established technique for the controlled deposition of a variety of substrates. For example, an Edwards Vapor deposition module allows the deposition of an inert coating of $SiO_2$. Further, a dielectric layer may include $MgF_2$ or $CaF_2$.

A still further aspect of the invention relates to a bioassay for measuring concentration of receptor-ligand binding in a test sample, the method comprising:
a) providing a substrate comprising multiple layers of metallic nanoparticles, wherein the metallic nanoparticles positioned on the top surface of the multiple layers have attached thereto a receptor molecule having affinity for a ligand of interest;
b) contacting the receptor molecule with the test sample suspected of comprising the ligand of interest, wherein the ligand of interest will bind to the receptor molecule to form a receptor-ligand complex;
c) contacting the receptor-ligand complex with a detector molecule having affinity for the ligand to form a receptor-ligand-detector complex, wherein the detector molecule comprises a first component of a bioluminescence or chemiluminescence generating system;
d) exposing the first component of the bioluminescence or chemiluminescence generating system to a trigger solution comprising a second component that will chemically react with the first component to induce a chemically electronically excited state; and
e) measuring the radiation emitted from exited metallic surface plasmons and/or test sample.

Preferably, the components of the bioluminescence generating system are a luciferase and a luciferin. The bioluminescence generating system may be selected from the group consisting of those isolated from the ctenophores, coelenterases, mollusca, fish, ostracods, insects, bacteria, a crustacea, annelids, and earthworms. The luciferase may be selected from the group consisting of *Aequorea*, Vargula, *Renilla*, Obelin, Porichthys, Odontosyllis, Aristostomias, Pachystomias, firefly, and bacterial systems.

In another aspect the present invention relates to a system for generating electrical current, the system comprising:
a) a substrate comprising multiple layers of immobilized metallic nanoparticles wherein the top layer of metallic nanoparticles are at least partially covered with a polar solution;
b) a set of electrodes communicatively contacting at least some of the metallic nanoparticles; and
c) an intrinsic or extrinsic fluorophore positioned near the metallic nanoparticles positioned on the exposed top layers, wherein when the fluorophore is excited by electromagnetic energy a mirror dipole is induced in the metallic nanoparticles causing plasmonic current flow for storage, directing to a current reading device or to provide sufficient amperage to power a device.

In a still further aspect, the present invention relates to an assay using High Throughput Screening (HTS), the method comprising:
a) providing a well plate used in HTS systems comprising a multiplicity of wells, wherein the wells comprise multiple layers of immobilized metallic nanoparticles, wherein the metallic nanoparticles positioned on the top surface of the multiple layers are coupled to a binding receptor having affinity for a target molecule;
b) introducing at solution suspected of including the target molecule for binding to the binding receptor;
c) applying electromagnetic energy; and
d) measuring the plasmonic emissions from the system during a predetermined time period.

If polarization of the plasmonic emissions is being measured, the polarization values decrease as the binding of the target molecule increases.

For use in HTS plates, such as coated on 96-well and 384 well plates, the multiple layers of discretely sized metallic nanoparticles increase the brightness of close proximity fluorophore and photostability as well as the dwell time for sampling the luminescence in a well. The wells of the HTS plates may include optional sizes and shapes including cylindrical with a consistent diameter through the depth of the well or in the alternative have a conical shape wherein the diameter is reduced from the top of the well to the bottom.

In a still further aspect the present invention provides for a photosensitizer complex that enhances generation of singlet oxygen in molecular oxygen comprising:
a) a surface substrate comprising multiple layers of metallic nanoparticles, wherein the metallic nanoparticles positioned on the top surface of the multiple layers exhibit surface plasmons on excitation; and
b) a photosensitizer compound coupled to the metallic nanoparticles, wherein the photosensitizer compound is positioned at a distance from the metallic nanoparticles to provide for coupling interaction between the photosensitizer compound and excited metallic surface plasmons, thereby generating singlet oxygen in adjacent molecular oxygen.

Other aspects and advantages of the invention will be more fully apparent from the ensuing disclosure and appended claims.

DETAILED DESCRIPTION OF THE INVENTION

Figure 1:
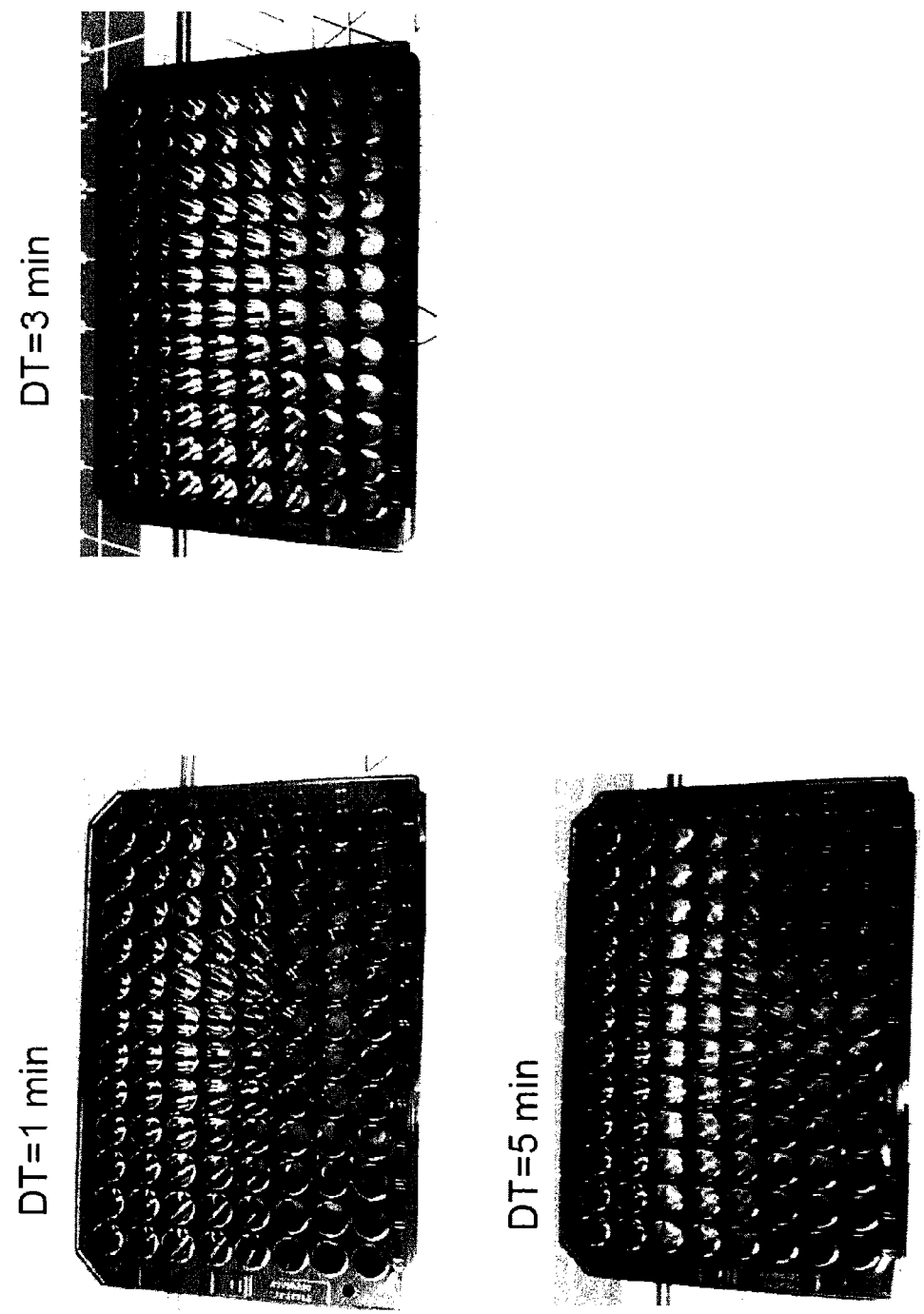
FIG. 1 shows that the color of the multilayers of nanoparticles depends on the size and density of the metal nanoparticles. Deposit time (DT) 1, 2 and 3 minutes.

The present invention relates to a method for fabricating a new silver coating/nanoparticle scaffold that significantly enhances the luminescence of near-field fluorophores via the metal enhanced fluorescence phenomenon. The silver coating/nanoparticle scaffold can be used for numerous applications in metal-enhanced fluorescence.

The present invention relates to a new process of depositing tunable sized nanoparticles on preformed substrates. As the nanoparticles are deposited upon previous layers, the spacers between the pre-existing particles are filled. As a function of increasing number of layers, the surfaces within the wells becomes highly polished, shiny and depending on the layer size and number, will have a different color. It is important to note, that the enhancement of intensity of emissions can be in the 1000's, for chemiluminescence and between 40-100 fold for fluorescence. The enhanced fluorescence is due to the MEF effect and the specific overlap of plasmon modes with the emission spectra of the fluorophore. This overlap integral of fluorophore emission and the scattering portion of the metallic nanoparticles extinction has until now been very difficult to measure, as hither to, there was no way to experimentally measure the scattering mode of the metal.

Specifically the new metallized surfaces may be used in numerous systems and methods including those described in U.S. patent application Ser. No. 10/536,502 entitled HIGH-SENSITIVITY ASSAYS FOR PATHOGEN DETECTION USING METAL ENHANCED FLUORESCENCE; U.S. patent application Ser. No. 11/917,804 entitled METAL-ENHANCED FLUORESCENCE-BASED SENSING METHODS; U.S. patent application Ser. No. 11/718,560 entitled METAL-ENHANCED FLUORESCENCE FROM PLAS- TIC SUBSTRATES; U.S. patent application Ser. No. 11/719,731 entitled MICROWAVE ACCELERATED ASSAYS; U.S. patent application Ser. No. 11/695,397 entitled MICROWAVE ACCELERATED PLASMONICS; International Patent Application No. PCT/US08/65801 entitled FLUORESCENCE MICROWAVE MICROSCOPY; U.S. patent application Ser. No. 12/036,402 entitled MICROWAVE FOCUSED CHEMILUMINESCENCE; U.S. patent application Ser. No. 11/750,119 entitled ANGULAR DEPENDENT METAL-ENHANCED FLUORESCENCE; U.S. patent application Ser. No. 12/020,571 entitled METAL-ENHANCED SINGLET OXYGEN GENERATION; U.S. patent application Ser. No. 11/917,075 entitled BIOASSAYS USING PLASMONIC SCATTERING FROM NOBLE METAL NANOSTRUCTURES; and U.S. patent application Ser. No. 11/997,778 entitled NANOSTRUCTURES FOR POLARIZED IMAGING AND RECEPTOR/LIGAND QUANTIZATION, the contents of such applications are hereby incorporated by reference herein for all purposes.

It must be noted that, as used in this specification and the appended claims, the singular forms "a," "an," and "the" include plural references unless the content clearly dictates otherwise.

The term "biomolecule" means any carbon based molecule occurring in nature or a derivative of such a molecule. The biomolecule can be in active or inactive form. "Active form" means the biomolecule is in a form that can perform a biological function. "Inactive form" means the biomolecule must be processed either naturally or synthetically before the biomolecule can perform a biological function. Exemplary biomolecules include nucleic acids, aromatic carbon ring structures, NADH, FAD, amino acids, carbohydrates, steroids, flavins, proteins, DNA, RNA, oligonucleotides, peptide nucleic acids, fatty acids, sugar groups such as glucose etc., vitamins, cofactors, purines, pyrimidines, formycin, lipids, phytochrome, phytofluor, peptides, lipids, antibodies and phycobiliproptein.

The term "receptor-ligand" as used herein means any naturally occurring or unnaturally occurring binding couple wherein the components have affinity for each other. For example, the binding couple may include an antibody/antigen complex, viral coat ligand/protein cell receptor or any combination of probe and binding partner. The term "receptor" refers to a chemical group, molecule, biological agent, naturally occurring or synthetic that has an affinity for a specific chemical group, molecule, virus, probe or any biological agent target in a sample. The choice of a receptor-ligand for use in the present invention will be determined by nature of the disease, condition, infection or specific assay.

"Fluorophore," and "fluorescence label," used interchangeably herein, means any substance that emits electromagnetic energy such as light at a certain wavelength (emission wavelength) when the substance is illuminated by radiation of a different wavelength (excitation wavelength) and is intended to encompass a chemical or biochemical molecule or fragments thereof that is capable of interacting or reacting specifically with an analyte of interest in a sample to provide one or more optical signals. Additionally fluorophore includes both extrinsic and intrinsic fluorophores. Extrinsic fluorophore refer to fluorophores bound to another substance. Intrinsic fluorophores refer to substances that are fluorophores themselves. Exemplary fluorophores include but are not limited to those listed in the Molecular Probes Catalogue which is incorporated by reference herein.

Representative fluorophores include but are not limited to Alexa Fluor® 350, Dansyl Chloride (DNS-Cl), 5-(iodoacetamida)fluoroscein (5-IAF); fluoroscein 5-isothiocyanate (FITC), tetramethylrhodamine 5-(and 6-)isothiocyanate (TRITC), 6-acryloyl-2-dimethylaminonaphthalene (acrylodan), 7-nitrobenzo-2-oxa-1,3,-diazol-4-yl chloride (NBD-Cl), ethidium bromide, Lucifer Yellow, 5-carboxyrhodamine 6G hydrochloride, Lissamine rhodamine B sulfonyl chloride, Texas Red™ sulfonyl chloride, BODIPY™, naphthalamine sulfonic acids including but not limited to 1-anilinonaphthalene-8-sulfonic acid (ANS) and 6-(p-toluidinyl)naphthalene-2-sulfonic acid (TNS), Anthroyl fatty acid, DPH, Parinaric acid, TMA-DPH, Fluorenyl fatty acid, Fluorescein-phosphatidylethanolamine, Texas red-phosphatidylethanolamine, Pyrenyl-phophatidylcholine, Fluorenyl-phosphotidylcholine, Merocyanine 540, 1-(3-sulfonatopropyl)-4[-.beta.-[2[(di-n-butylamino)-6naphthyl]vinyl]pyridinium betaine (Naphtyl Styryl), 3,3'dipropylthiadicarbocyanine (diS—$C_3$-(5)), 4-(p-dipentyl aminostyryl)-1-methylpyridinium (di-5-ASP), Cy-3 Iodo Acetamide, Cy-5-N-Hydroxysuccinimide, Cy-7-Isothiocyanate, rhodamine 800, IR-125, Thiazole Orange, Azure B, Nile Blue, Al Phthalocyanine, Oxaxine 1,4',6-diamidino-2-phenylindole (DAPI), Hoechst 33342, TOTO, Acridine Orange, Ethidium Homodimer, N(ethoxycarbonylmethyl)-6-methoxyquinolinium (MQAE), Fura-2, Calcium Green, Carboxy SNARF-6, BAPTA, coumarin, phytofluors, Coronene, and metal-ligand complexes.

Representative intrinsic fluorophores include but are not limited to organic compounds having aromatic ring structures including but not limited to NADH, FAD, tyrosine, tryptophan, purines, pyrimidines, lipids, fatty acids, nucleic acids, nucleotides, nucleosides, amino acids, proteins, peptides, DNA, RNA, sugars, and vitamins. Additional suitable fluorophores include enzyme-cofactors; lanthanide, green fluorescent protein, yellow fluorescent protein, red fluorescent protein, or mutants and derivates thereof.

Fluorophores with high radiative rates have high quantum yields and short lifetimes. Increasing the quantum yield requires decreasing the non-radiative rates $k_{nr}$, which is often only accomplished when using a low solution temperature or a fluorophore bound in a more rigid environment. The natural lifetime of a fluorophore, $\tau_n$, is the inverse of the radiative decay rate or the lifetime which would be observed if their quantum yields were unity. This value is determined by the oscillator strength (extinction coefficient) of the electronic transition. Hence, for almost all examples currently employed in fluorescence spectroscopy, the radiative decay rate is essentially constant. The modification and control of the radiative rate have also been referred as Radiative Decay Engineering (RDE), or "lightening rod" fluorescence enhancement effect. For example, enhanced intrinsic DNA fluorescence above metallic particles has recently been observed, which is typically not readily observable because of DNA's very low quantum yield of less than $10^{-4}$. The second favorable "lightening rod" effect also increases the fluorescence intensity by locally enhanced excitation. In this case, emission of fluorophores can be substantially enhanced irrespective of their quantum yields.

The reduction in lifetime of a fluorophore near a metal is due to an interaction between the fluorophore and metal particle, which enhances the radiative decay rate (quantum yield increase) or depending on distance, $d^{-3}$, causes quenching. It should be noted that lifetimes of fluorophores with high quantum yields (0.5) would decrease substantially more than the lifetimes of those with low quantum yields (0.1 and 0.01). A shorter excited-state lifetime also allows less photochemical reactions, which subsequently results in an increased fluorophore photostability. Notably, the use of low quantum yield fluorophores would lead to much larger fluorescence enhancements (i.e. $1/Q_0$) and could significantly reduce unwanted background emission from fluorophores distal from the silvered assay.

Fluorophore photostability is a primary concern in many applications of fluorescence. This is particularly true in single molecule spectroscopy. A shorter lifetime also allows for a larger photon flux. The maximum number of photons that are emitted each second by a fluorophore is roughly limited by the lifetime of its excited state. For example, a 10 ns lifetime can yield about $10^8$ photons per second per molecule, but in practice, only $10^3$ photons can be readily observed. The small number of observed photons is typically due to both photo-destruction and isotropic emission. If a metal surface decreases the lifetime, one can obtain more photons per second per molecule by appropriately increasing the incident intensity.

On the other hand, the metal-enhanced fluorescence provides enhanced intensity, while simultaneously shortening the lifetime. That is, it may be possible to decrease the excitation intensity, yet still see a significant increase in the emission intensity and photostability.

The emission enhancement may be observed at distances according to the type of fluorophore to be detected and the type, shape of the metal material, noting a difference between a film and a metallic island or colloid. For example, emission enhancement may be observed when a fluorophore is positioned from about 5 nm to about 200 nm from the metal surfaces. Preferable distances are about 5 nm to about 30 nm, and more preferably, 5 nm to about 20 nm to metal surfaces. At this scale, there are few phenomena that provide opportunities for new levels of sensing, manipulation, and control. In addition, devices at this scale may lead to dramatically enhanced performance, sensitivity, and reliability with dramatically decreased size, weight, and therefore cost.

Attaching of the fluorophore to a probe may be achieved by any of the techniques familiar to those skilled in the art. For example, the fluorophore may be covalently attached to the bimolecular probe by methods disclosed in U.S. Pat. No. 5,194,300 (Cheung) and U.S. Pat. No. 4,774,189 (Schwartz).

In another embodiment, the assay system of the present invention provides for detecting and separating at least two target pathogen by choosing fluorophores such that they possess substantially different emission spectra, preferably having emission maxima separated by greater than 10 nm, more preferably having emission maxima separated by greater than 25 nm, even more preferably separated by greater than 50 nm. When differentiation between the two fluorophores is accomplished by visual inspection, the two dyes preferably have emission wavelengths of perceptibly different colors to enhance visual discrimination. When it is desirable to differentiate between the two fluorophores using instrumental methods, a variety of filters and diffraction gratings allow the respective emission maxima to be independently detected.

Any chemiluminescent species may be used in the present invention that provides for a chemical reaction which produces a detectable reaction (observed emission) wherein the excited state responsible for the observed emission including, but not limited to the following excitation mechanisms:

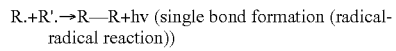
R.+R'.→R—R+hv (single bond formation (radical-radical reaction))

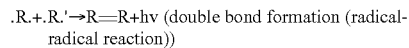
.R.+.R.'→R=R+hv (double bond formation (radical-radical reaction))

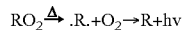
$RO_2 \xrightarrow{\Delta}$ .R.+$O_2$→R+hv

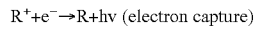
$R^+ + e^- \rightarrow$ R+hv (electron capture)

Examples of suitable chemiluminescence detector molecules include but without limitation, peroxidase, bacterial luciferase, firefly luciferase, functionalized iron-porphyrin derivatives, luminal, isoluminol, acridinium esters, sulfonamide and others. A recent chemiluminescent label includes xanthine oxidase with hypoxanthine as substrate. The triggering agent contains perborate, a Fe-EDTA complex and luminol. Choice of the particular chemiluminescence labels depends upon several factors which include the cost of preparing labeled members, the method to be used for covalent coupling to the detector molecule, and the size of the detector molecules and/or chemiluminescence label. Correspondingly, the choice of chemiluminescence triggering agent will depend upon the particular chemiluminescence label being used.

Chemiluminescent reactions have been intensely studied and are well documented in the literature. For example, peroxidase is well suited for attachment to the detector molecule for use as a chemiluminescence. The triggering agent effective for inducing light emission in the first reaction would then comprise hydrogen peroxide and luminol. Other triggering agents which could also be used to induce a light response in the presence of peroxidase include isobutyraldehyde and oxygen. Procedures for labeling detector molecules, such as antibodies or antigens with peroxidase are known in the art. For example, to prepare peroxidase-labeled antibodies or antigens, peroxidase and antigens or antibodies are each reacted with N-succinimidyl 3-(2-pyridyldithio) propionate (hereinafter SPDP) separately. SPDP-labeled peroxidase, or SPDP-labeled antigen or antibody is then reacted with dithiothreitol to produce thiol-labeled peroxidase, or thiol-labeled antigen or antibody. The thiol derivative is then allowed to couple with the SPDP-labeled antigen or antibody, or SPDP-labeled peroxidase.

The present invention further comprises a detection device for detecting emissions including, but not limited to visual inspection, digital (CCD) cameras, video cameras, photographic film, or the use of current instrumentation such as laser scanning devices, fluorometers, luminometers, photodiodes, quantum counters, plate readers, epifluorescence microscopes, fluorescence correlation spectroscopy, scanning microscopes, confocal microscopes, capillary electrophoresis detectors, or other light detector capable of detecting the presence, location, intensity, excitation and emission spectra, fluorescence polarization, fluorescence lifetime, and other physical properties of the fluorescent signal.

Excitation light sources can include arc lamps and lasers, natural sunlight, laser diodes and light emitting diode source, and both single and multiple photon excitation sources. In another embodiment, use of a Ti-sapphire laser, Laser Diode (LD) or Light Emitting Diode Sources (LEDs) may be used with the RNA assay of the present invention. For example, using 2-photon excitation at 700-1000 nm and also using short pulse width (<50 pi), high repetition rate (1-80 MHz), laser diode and LED (1 ns, 1-10 MHz) sources. The enhanced sensitivity of the assay using 2-photon excitation, as compared to 1-photon, can be shown by using series dilution with RNA, initially with the Ti-Sapphire system, and later with LEDs and LDs. If a fluorophore absorbs two photons simultaneously, it will absorb enough energy to be raised to an excited state. The fluorophore will then emit a single photon with a wavelength that depends on the fluorophore used and typically in the visible spectra. The use of the Ti-sapphire laser with infrared light has an added benefit, that being, longer wavelengths are scattered less, which is beneficial for high-resolution imaging. Importantly, there is reduced background signal level gained by using 2-photon excitation as compared to 1-photon excitation by utilizing localized excitation nearby metallic nanoparticles.

In another embodiment, the present invention relates to detection of a nucleotide sequence. The nucleotide sequence communicatively connect to the metallic material can be quantified compared to the undetectable emission on non-metallized surface. In this regard, the detection of RNA is accomplished by annealing a target RNA, tagged with a fluorophore, to an oligonucleotide anchor probe in a single step on a solid surface, where the, fluorescence signal is intrinsically enhanced by silver nanoparticles.

"Nucleotide," as used herein refers to deoxyribonucleic acid (DNA) or ribonucleic (RNA), RNA can be unspliced or spliced mRNA, rRNA, tRNA, or antisense RNAi. DNA can be complementary DNA (cDNA), genomic DNA, or an antisense.

The nucleotides used as hybridization probes in the present invention are typically designed to be specific for the desired sequence in order to decrease the probability of hybridizing to unrelated sequences. Such probes can be modified so as to be detectable using radionuclides, luminescent moieties, and so forth. Hybridization conditions also can be modified in order to achieve the desired specificity. For example, a moderately stringent hybridization condition may include: 2×SSC/0.1% SDS at about 37° C. or 42° C. (hybridization conditions); 0.5×SSC/0.1% SDS at about room temperature (low stringency wash); 0.5×SSC/0. 1% SDS at about 42° C. (moderate stringency wash). An example of moderately-high stringency hybridization conditions is as follows: 0.1×SSC/0.1% SDS at about 52° C. (moderately-high stringency wash). An example of high stringency hybridization conditions is as follows: 0.1×SSC/0.1% SDS at about 65° C. (high stringency wash).

The nucleotides sequences of the present invention can be obtained using standard techniques known in the art (e.g., molecular cloning, chemical synthesis) and the purity can be determined by polyacrylamide or agarose gel electrophoresis, sequencing analysis, and the like. Polynucleotides also can be isolated using hybridization or computer-based techniques that are well known in the art. Such techniques include, but are not limited to: (1) hybridization of genomic DNA or cDNA libraries with probes to detect homologous nucleotide sequences; (2) antibody screening of polypeptides expressed by DNA sequences (e.g., using an expression library); (3) polymerase chain reaction (PCR) of genomic DNA or cDNA using primers capable of annealing to a nucleic acid sequence of interest; (4) computer searches of sequence databases for related sequences; and (5) differential screening of a subtracted nucleic acid library.

In another embodiment, the application of low level microwave heating of the sample may be used to speed up any chemical/biochemical kinetics within the system. Notably, low level microwaves do not destroy or denature proteins, DNA, or RNA, but instead heat the sample sufficiently to provide for accelerated kinetics such as binding or hybridization. In addition, the microwaves are not scattered by the metallic nanoparticles, which is contrary to most metal objects, such as that recognized by placing a spoon in a microwave oven.

Microwaves (about 0.3 to about 300 GHz) lie between the infrared and radiofrequency electromagnetic radiations. It is widely thought that microwaves accelerate chemical and biochemical reactions by the heating effect, where the heating essentially follows the principle of microwave dielectric loss. Polar molecules absorb microwave radiation through dipole rotations and hence are heated, where as non-polar molecules do not absorb due to lower dielectric constants are thus not heated. The polar molecules align themselves with the external applied field. In the conventional microwave oven cavity employed in this work, the radiation frequency (2450 MHz) changes sign $2.45 \times 10^9$ times per second. Heating occurs due to the torsional effect as the polar molecules rotate back and forth, continually realigning with the changing field, the molecular rotations being slower than the changing electric field. The dielectric constant, the ability of a molecule to be polarized by an electric field, indicates the capacity of the medium to be microwave heated. Thus, solvents such as water, methanol and dimethyl formamide are easily heated, whereas microwaves are effectively transparent to hexane, toluene and diethylether. For metals, the attenuation of microwave radiation arises from the creation of currents resulting from charge carriers being displaced by the electric field. These conductance electrons are extremely mobile and unlike water molecules can be completely polarized in 10-18 s. In microwave cavity used in the present invention, the time required for the applied electric field to be reversed is far longer than this, in fact many orders of magnitude. If the metal particles are large, or form continuous strips, then large potential differences can result, which can produce dramatic discharges if they are large enough to break down the electric resistance of the medium separating the large metal particles. Interestingly, and most appropriate for the new assay platform described herein, small metal particles do not generate sufficiently large potential differences for this "arcing" phenomenon to occur. However, the charge carriers which are displaced by the electric field are subject to resistance in the medium in which they travel due to collisions with the lattice phonons. This leads to Ohmic heating of the metallic structures in addition to the heating of any surface polar molecules. Intuitively, this leads to localized heating around the metallic structures in addition to the solvent, rapidly accelerating assay kinetics.

In the present invention, microwave radiation may be provided by an electromagnetic source having a frequency in a range between 0.3 and 10 GHz and a power level in a range between about 10 mwatts and 400 watts, more preferably from 30 mwatts to about 200 watts. Any source, known to one skilled in the art may be used, such as a laser that emits light, wherein light is used in its broad sense, meaning electromagnetic radiation which propagates through space and includes not only visible light, but also infrared, ultraviolet and microwave radiation. Thus, a single instrument placed above the surface of the assay can be used to generate the microwave energy and energy to excite fluorescing molecules. The light can be emitted from a fiber continuously or intermittently, as desired, to maintain the metallic particles at a predetermined temperature such that it is capable of increasing the speed of chemical reactions within the assay system. The microwave radiation may be emitted continuously or intermittently (pulsed), as desired. In the alternative, microwave energy can be supplied through a hollow wave guide for conveying microwave energy from a suitable magnetron. The microwave energy is preferably adjusted to cause an increase of heat within the metallic material without causing damage to any biological materials in the assay system.

Although fluorescence, chemiluminescence and/or bioluminescence detection has been successfully implemented, the sensitivity and specificity of these reactions require further improvements to facilitate early diagnosis of the prevalence of disease. In addition, most protein detection methodologies, most notably western blotting, are still not reliable methods for accurate quantification of low protein concentrations without investing in high-sensitivity detection schemes. Protein detection methodologies are also limited by antigen-antibody recognition steps that are generally kinetically very slow and require long incubation times; e.g., western blots require processing times in excess of 4 h. Thus, both the rapidity and sensitivity of small-molecule assays are still critical issues to be addressed to improve assay detection. As such the use of low intensity ultrasound will increase the rapidity of the assay.

There are many important assays that can directly benefit from enhanced signal intensities and quicker kinetics. For example, myoglobin concentrations for heart attack patients, patients of toxic shock and pancreatitis. All of these assays are widely used in hospitals emergency rooms with assay times of greater than 30 minutes. Thus, the present invention can be used for points-of-care clinical assessment in emergency rooms.

Thus it would be advantageous to increase speed of any chemical or biochemical reaction by using any device capable of generating and transmitting acoustic energy through any medium to transit ultrasonic atomizing energy. The ultrasonic emitting device can be placed in either the interior of a vessel used in a detection system or positioned adjacent thereto for transmitting energy into the vessel. The device may include components for the traditional electromagnetic stimulation of piezoelectric transducers, (man-made or naturally occurring), purely mechanical devices (such as high frequency air whistles or microphones), and laser devices. Individual components for acoustic energy systems are commercially available from a wide variety of manufacturers, which can be configured to particular applications and frequency ranges. (See Thomas Directory of American Manufacturers, Photonics Buyer's Guide, 1996, Microwave and RF, and Electronic Engineer's Master Catalogue).

Any oscillator or signal generator that produces a signal with predetermined characteristics such as frequency, mode, pulse duration, shape, and repetition rate may be used to generate acoustic frequencies for applying to the system of the present invention. Various oscillators or signal generators can be commercially purchased from a wide variety of manufacturers and in a variety of designs configured to particular applications and frequencies. Applicable transducers will include types that produce an acoustic wave within a range of frequencies (broadband) or for one specific frequency (narrowband) for frequencies ranging from hertz to gigahertz.

The acoustic delivery system will be variable depending on the application. For example, acoustic energy waves can be transmitted into liquid or solid source material either by direct contact of the source material with a transducer, or by coupling of transmission of the acoustic wave through another medium, which is itself in direct contact with the source material. If the source material is a liquid, a transducer can be placed in the liquid source material, or the walls of the vaporization vessel can be fabricated of a material that acts as a transducer thereby placing the liquid source material in direct contact with the transducer. Additionally, an acoustic energy emitting device may be positioned on the exterior of a system container for transmitting the appropriate energy. If the source material is a solid, a transducer can be placed in direct contact with it or the solid source material can be placed in a gas or liquid that is used as a coupling agent.

In the preferred acoustic frequencies any system that generates acoustic energy may be utilized. Preferably, the output of the ultrasonic generator is of a sufficient frequency to provide a movement flow within the system vessel to move molecules to the source of binding or reaction site without causing a large increase of heat in the system. For example, using the power output of 0.5 to 50 W at a frequency of 10 to 200 kHz, and more preferably from about 20 to 60 kHz and most preferably at about 40 kHz.

To obtain the maximum transfer of acoustical energy from one medium to another, the characteristic acoustical impedance of each medium is preferably as nearly equal to the other as possible. The matching medium is sandwiched between the other two and should be the appropriate thickness relative to the wavelength of the sound transmitted, and its acoustical impedance R should be nearly equal to $(R_1:R_2)$. Any impedance matching device that is commercially available can be utilized in the present invention.

The system may include ultrasonic vessels wherein at least a section of the vessel includes a transducer such as a piezoelectric transducer to generate acoustic vibrations. Such transducers can be located in the bottom of a vessel or in a plate whereon a vessel may be placed. Further such transducers can be placed at different levels on the vessel walls to enhance fluid flow within the vessel.

EXAMPLES

Preparation of Substrate with Multiple Layers of Metallized Nanoparticles.

The following reagents were used to prepare solutions for silver deposition on plate well's bottom: 1.245% $AgNO_3$; 10% NaOH; $NH_4OH$ (30%) and 7.5% Glucose.

There are two separate solutions made, one in a 500 ml flash and another in an 80 ml flash.

In a 500 ml beaker, for preparation of a single plate, add 15 ml of 1.245% $AgNO_3$ to the 500 ml flask with a stir bar and place the flask on the stirring plate. While the solution is stirring, add 750 μl of 10% NaOH that results in formation of brown precipitate. Subsequently, add 4 ml of $NH_4OH$ drop-wise to allow for precipitate to dissolve. Cover the flask with aluminium foil and keep it on ice for at least 10 min prior the experiment.

In an 80 ml beaker with a stir bar, add 15 ml of 1.66% $AgNO_3$. Place the beaker on a stirring plate and add 100 μl of 10% NaOH, allowing brown precipitate to form. Then, add 450 μl of $NH_4OH$, and place beaker on ice for 10 min.

The plate may be treated in plasma cleaner prior the experiment to be sure that the surface is hydrophilic. For example, place the substrate into a plasma cleaner, turn on vacuum pump and leave it under vacuum for 10 minutes. Then turn on Plasma cleaner on medium for another 10 minutes.

For initial deposition, use the solution prepared in 80 ml beaker. Place the beaker on the stirring plate and add 3.75 ml of 10% w/v Glucose. Immediately, process with addition of 200 μl of the solution into each well. Place the plate on a heat-block for 2 min at 50° C., covered with metal block, then transfer it to the freezing camera for 2 min, and back to the heat-block for 1.5 min. Discard solution from the wells and wash the plate with deionized water.

For the next 10 layers (silver depositions), use the solution prepared in the 500 ml conical flask. Set up ten 80 ml beakers on the side. For each deposition, add 15 ml of the solution into the beaker with a stir bar, and place the beaker onto the stirring plate. Subsequently, add 2.8 ml of 10% Glucose, and immediately process with addition of 200 μl of the obtained solution in each well. Place the plate on the heat block for 3 min at 50° C., skipping the step with refrigeration. Discard solution from the wells and wash the plate with DI water. Repeat the step according to the total deposition time required (about 30 min).

Another composition solution for fabrication is set forth below:

Materials:

Clean and oven dried 100 ml beaker $AgNO_3$ (1.25% w/v)

NaOH (10% w/v)
NH$_4$OH (30% from stock)
D-glucose solution (7.2% w/v)
Plasmon cleaner
96 well plate
All solutions should be kept cold on 4° C.
Procedure
Cleaning
Fill in ice in the ice chamber attached to vacuum pump
Place the 96 well-plate in to Plasma cleaner
Turn on vacuum pump and leave it under vacuum for 10 minutes
Turn on Plasmon cleaner on medium for another 10 minutes
Covering with Silver
Turn block heater on 42° C.
Poor 20 ml of Silver Nitrate in clean glass beaker
Add 75 uL of Sodium Hydroxide in to the beaker while stirring (solution should become turbid)
Add 600 uL Ammonium hydroxide in to the beaker (solution should become clear again)
Add 4.9 ml of Glucose in solution.
Transfer solution in to wells (240 uL each well) and place it to the block heater
First layer: 2 min heater followed by 2 min freezer and 2 min heater
Dump old solution and wash plate with DI water
Second through 12 layer is preferably should be 3 minutes on heater.

FIG. 1 shows deposition colors for the layers of metallic nanoparticles wherein the color is dependent on the size of the particles and number of layers. The deposition time (DT) of 1 minute provides a blue color, deposition time of three minutes provides a gold color and five minutes of deposition provides a red color. Thus, as the density increases on the substrate the reflection of excitation energy changes from the blue wavelength range to the shorter red wavelength. Notably as the particle size increases there is a red shift in emitted wavelengths.

Figure 2:
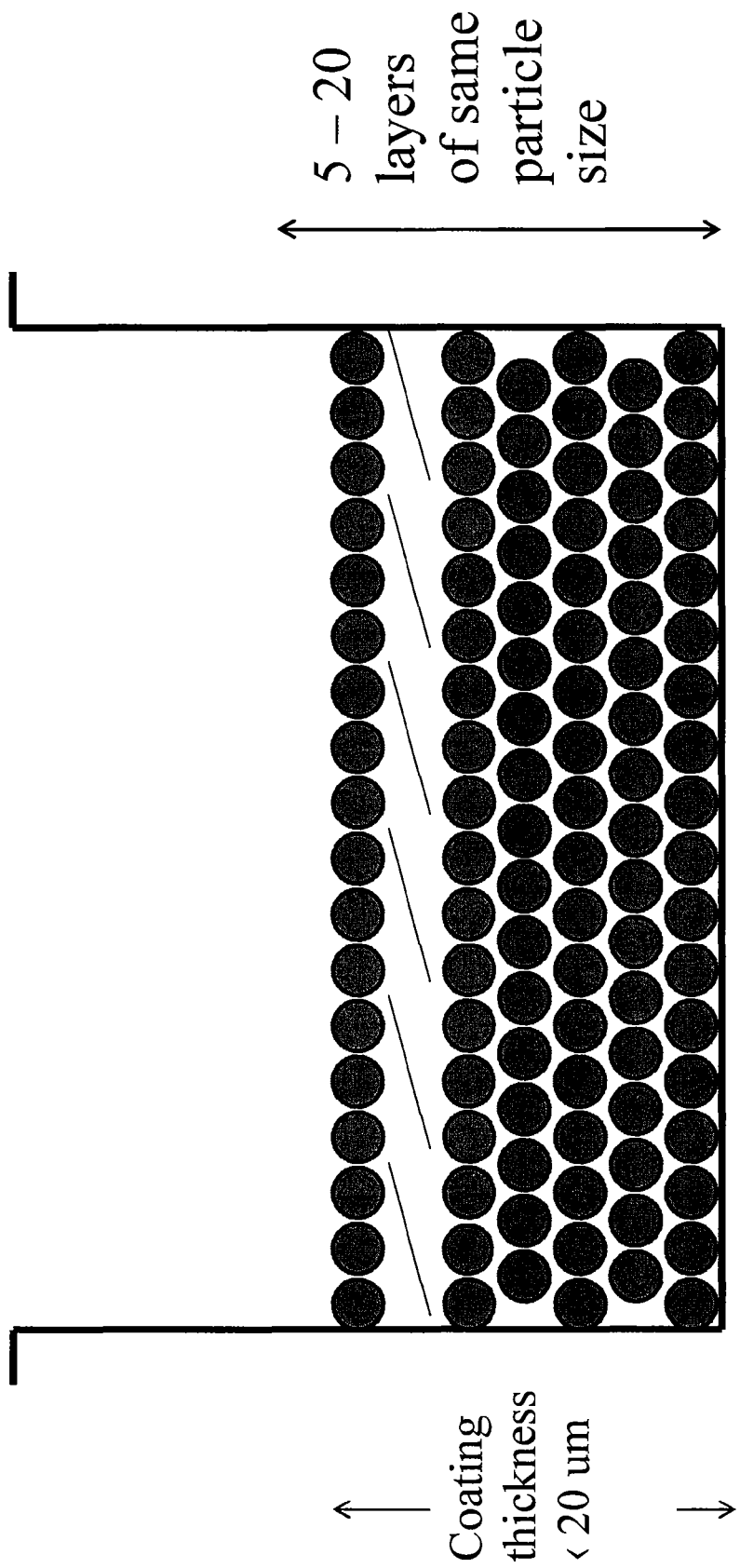
FIG. 2 shows a container comprising multiple layers of discrete sized nanoparticles. Nanopolishing to grow/deposit nanoparticles of uniform particle sizes.

FIG. 2 is a representative illustration of a HTS plate well showing the depositing of multiple layers of the same size particles. Notably such a container having the multiple layers is similar to a container filled with ping pong balls, wherein voids of a previous layer are filled with nanoparticles on the next deposited layer.

Figure 3:
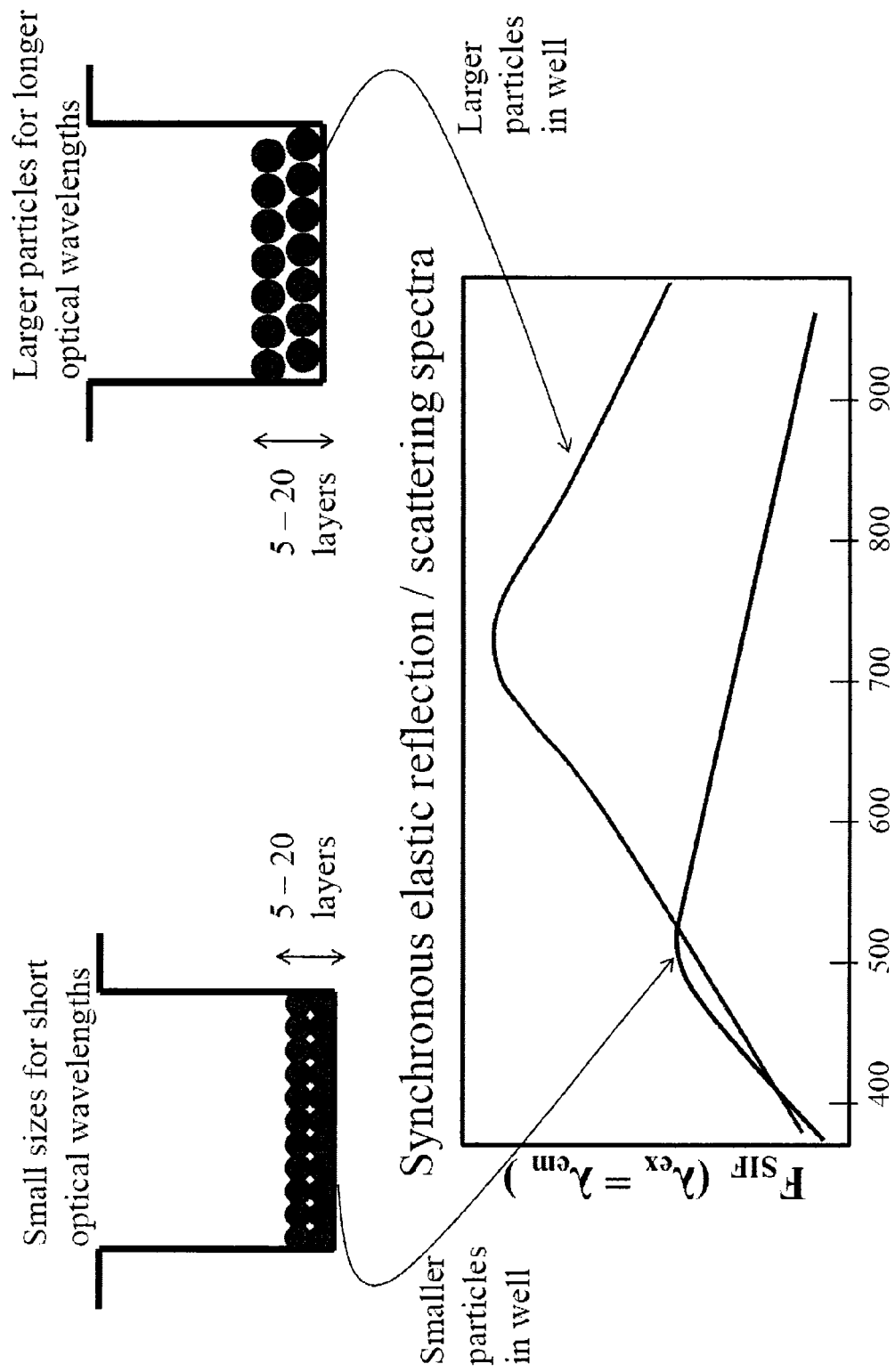
FIG. 3 shows layer of small sizes starting at merely two layers and larger particles also with only two layers. The synchronous elastic reflection/scattering spectra show different wavelengths for different sizes and as nanoparticles sizes increase there is a red shift.

FIG. 3 shows that particle size provides for distinct plots for synchronous elastic reflection/scattering spectra. Clearly the smaller particles provide for reflection/scattering in the 500 nm range explaining the blue refection discussed above. As the particles increase in size, the reflection/scattering spectra moves into the red range that being 700 nm. Using the spectroscopic technique, "Synchronous Scatter", enables to 1) To determine the extent of growth/deposition of the nanoparticles within the wells, 2) To determine what fluorophores will preferentially function with the plates and 3) as a predictor of the magnitude of the metal-enhanced fluorescence effect.

Figure 4:
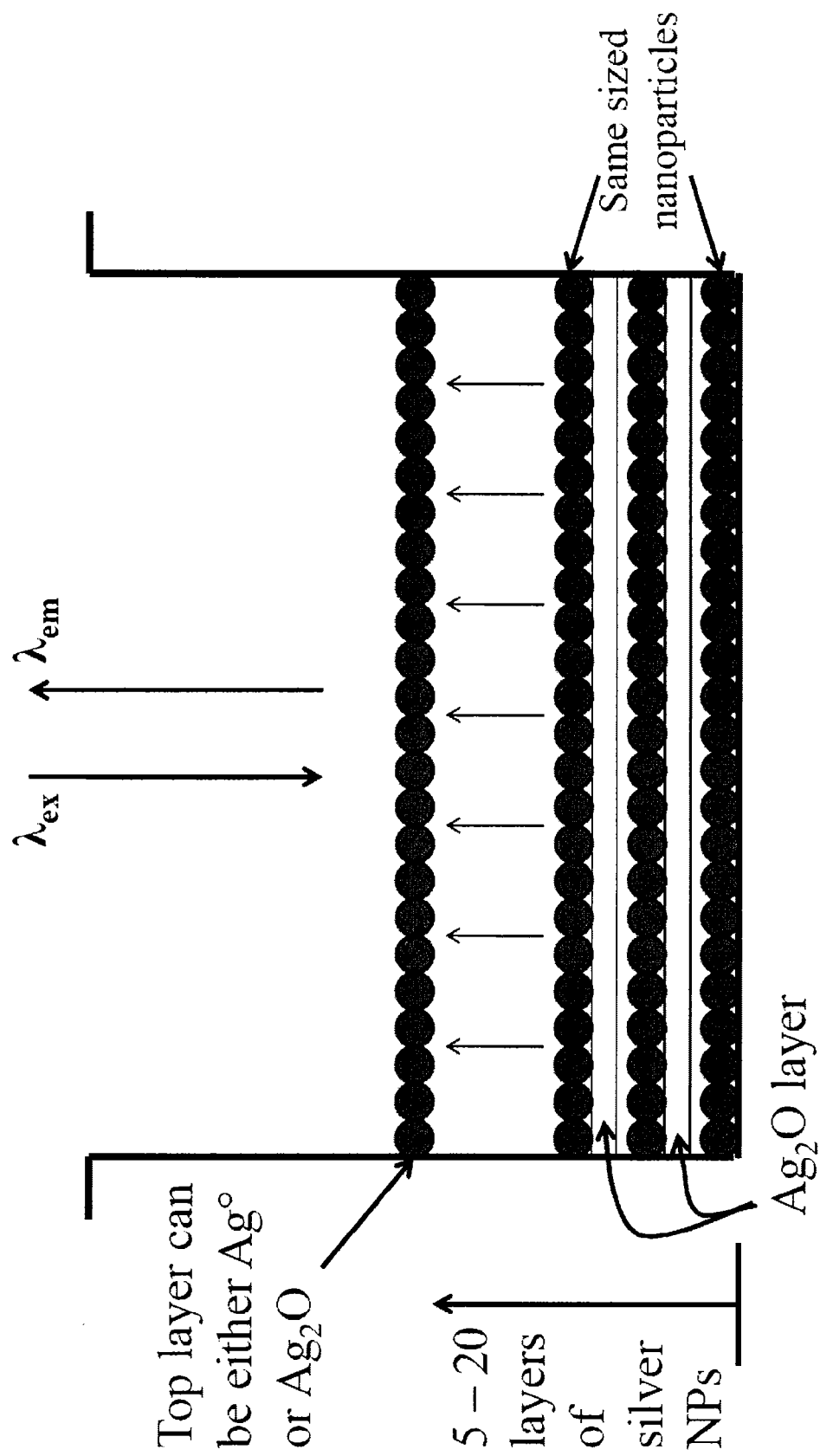
FIG. 4 shows the use of a dielectric layer positioned between the layers of nanoparticles.

FIG. 4 provides an illustration of a container showing the deposition of silver particles with a layer of metal oxide between each layer of nanoparticles.

Figure 5:
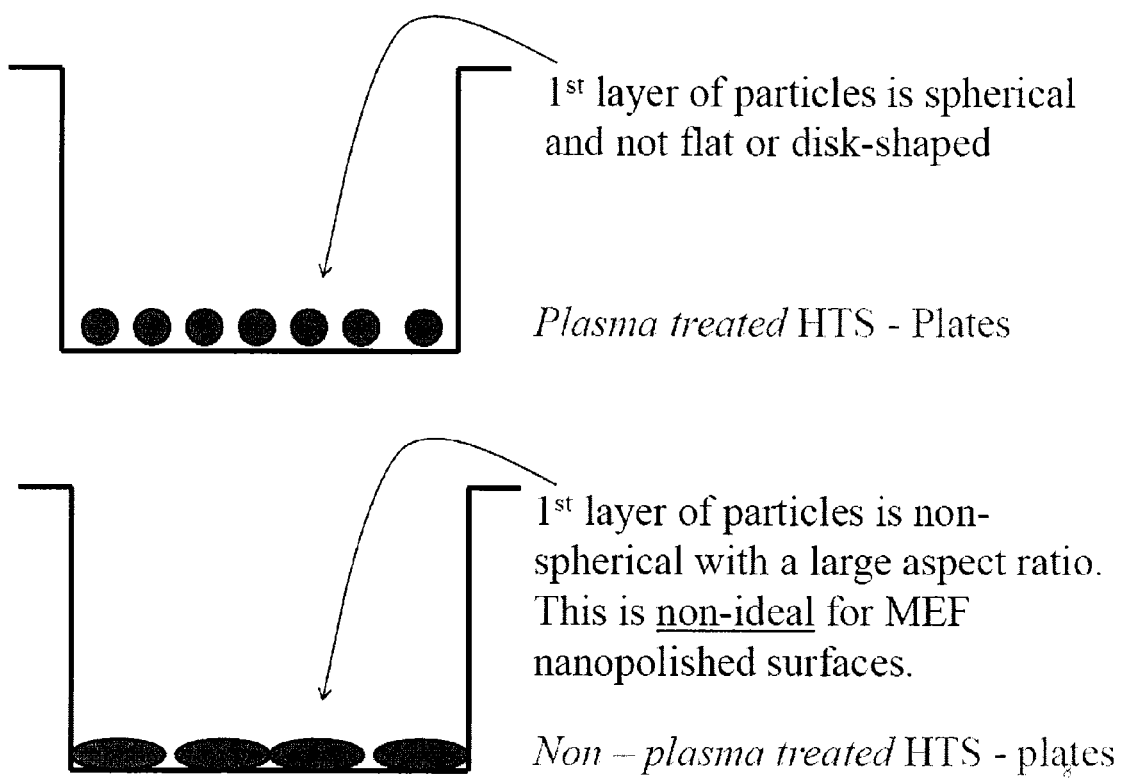
FIG. 5 shows the use of hydrophilic plastic surface is paramount for the depositing of the nanoparticles.

FIG. 5 shows the importance of pre-treating the surface for proper deposition of spherical particles. Control of surface properties is very important for the high performance of adhesion of the deposited nanoparticles. Surface modification of hydrophobic polymer surface into a hydrophilic surface can be achieved by wet (acid, alkali), dry (plasma) and radiation treatments (ultraviolet radiation and laser) without affecting the bulk properties. Glow discharge plasmas are generally used for the surface modification of polymers because the processes involved are solvent free and dry, the consumption of chemicals is extremely low and need for sterilization of the products is eliminated. Thus, if the surface substrate is fabricated of a hydrophobic material or a material that is not sufficiently hydrophilic, such as polystyrene or polyethylene, such polymeric materials may be plasma treated to provide a more hydrophilic surface. Such surfaces provide for the formation of spherical nanoparticles because non-spherical particles are not ideal for MEF nanopolished surfaces.

Figure 6:
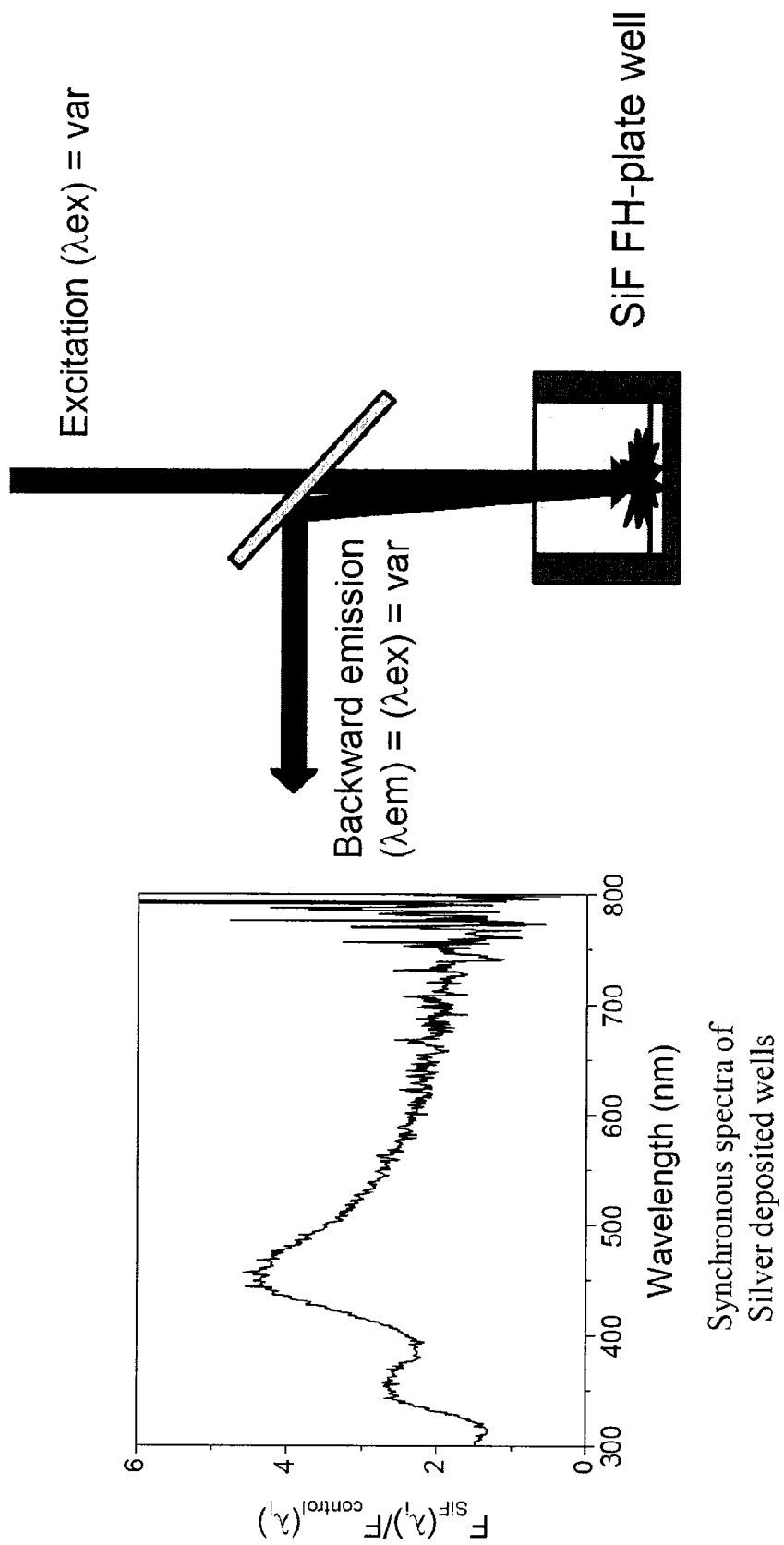
FIG. 6 shows the synchronous spectra of the multilayers of nanoparticles on a coated surface.

The present invention provides for a new method for measuring the scattering portion of the metal nanoparticles extinction spectrum, thereby providing a method for measuring the MEF efficiency of surfaces, and even a predictor of MEF without the necessity of physical measurements. In contrast to the optical Extinction Spectra of Silver nanodeposits, which is a sum of the absorption ($E_{abs}$) and plasmon scattering ($E_{Sca}$) components of nanoparticle extinction, synchronous spectra show plasmon-specific scattering component of the total spectra. FIG. 6 shows the synchronous spectra of silver coated surface with multiple layers.

Figure 7:
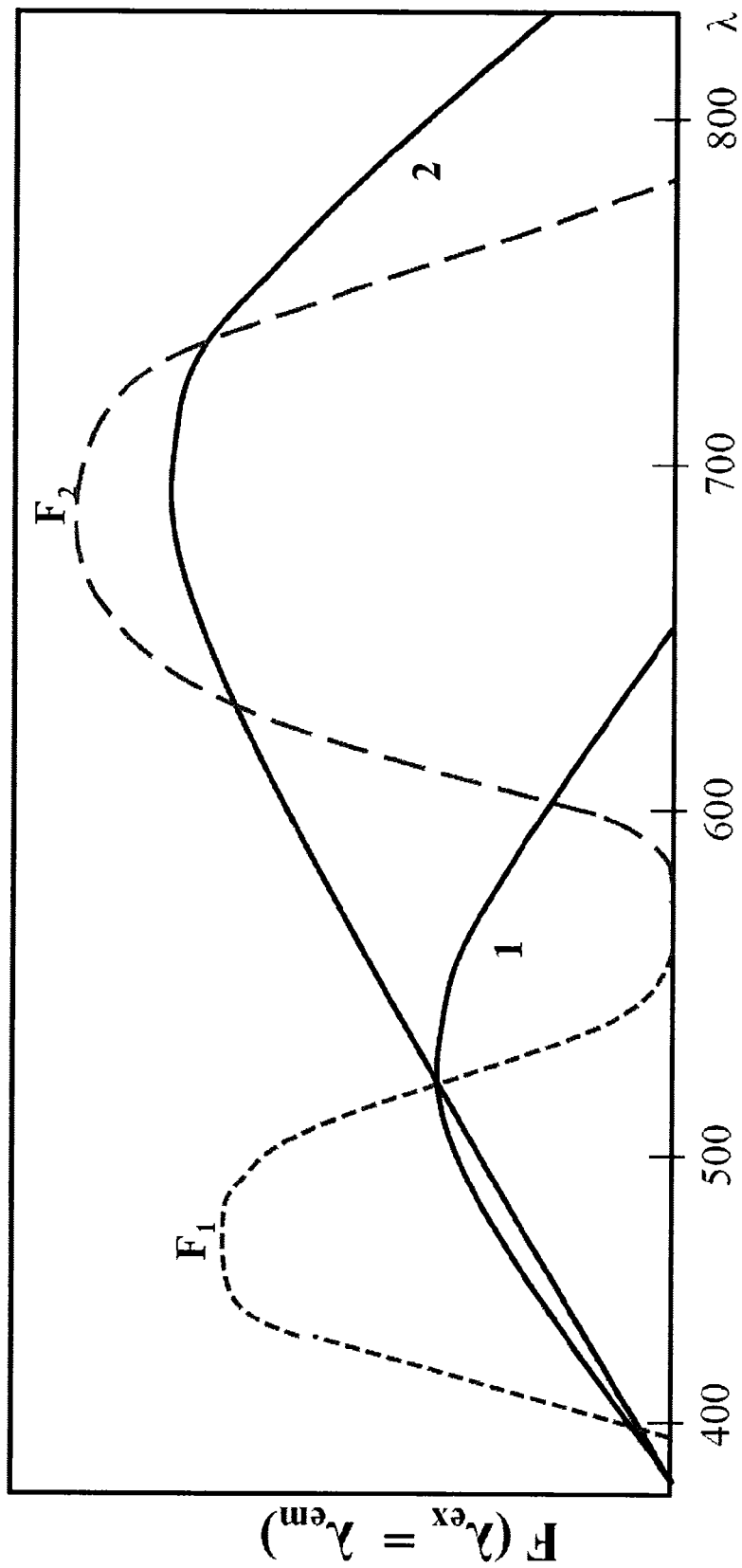
FIG. 7 shows the both the synchronous elastic scatter spectrum and fluorophore emission spectra for two different sized nanoparticles.

It is shown herein that the size of particles in wells can be tuned for maximum fluorescence/chemiluminescence enhancement. FIG. 7 shows the results of two testing samples wherein fluorescein is used as a fluorophore and positioned from about 5 nm to 25 nm from the top surface of the final layer of particles. The diameter of the nanoparticles in spectrum 1 is smaller than the nanoparticles of spectrum 2. $F_1$ and $F_2$ show the fluorophore emission spectral. Spectrum 1 is the synchronous elastic scatter spectrum for 8-15 layers of nanopolished surface while spectrum 2 is the synchronous elastic scatter spectrum for 8-15 layers of nanopolished surface. Particle sizes for spectrum 2 are much bigger that those in spectrum 1. Notably the degree of overlap of the fluorophore emission spectrum with the synchronous elastic scatter spectrum is a predictor of MEF and the specific size of the nanoparticle that is needed.

Figure 8:
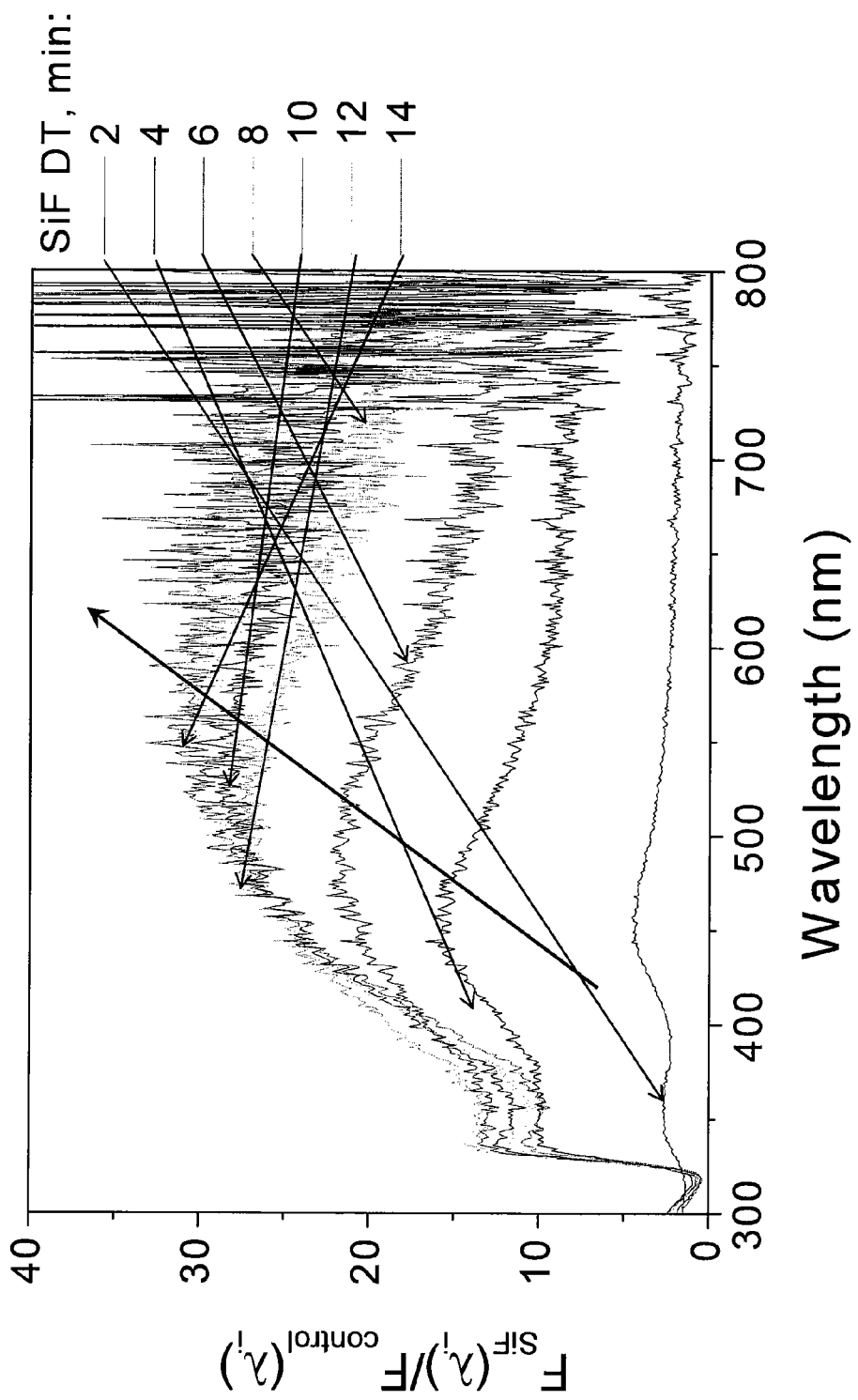
FIG. 8 shows the synchronous spectra from the bottom of a well comprising the multilayers of nanoparticles of the present invention.
Figure 9:
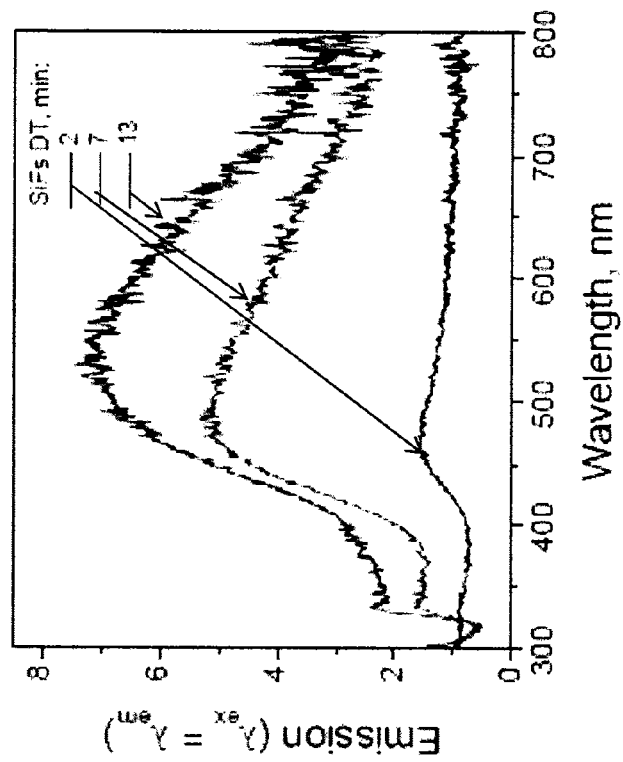
FIG. 9 shows the optical absorption and synchronous spectra of silver coated plates.
Figure 9:
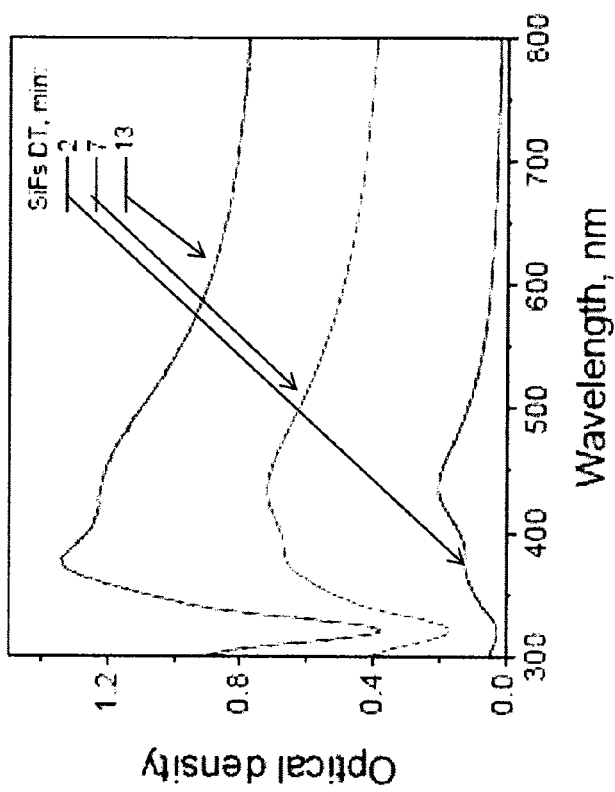

FIGS. 8 and 9 show the uniqueness of the multilayer nanoparticles when compared to silver films. As shown in FIG. 9 (right) the synchronous scattering spectrum from a SiFs film within a container grown for different periods of time, is very different from the synchronous spectra of the nanopolished multilayer surface, as shown in FIG. 8. It is this red shifted property of the plasmon scattering band which gives the plates their unique enhancing ability, as shown in FIG. 8. The key to nanopolishing is the multiple discrete layers of same size particles, grown in the voids of previous coating layers. Clearly, the synchronous spectra of FIG. 8 show efficiency and characteristics of specific nanoparticle size-dependent plasmon scattering of SiF in wells. Increase in nanoparticle size and density shifts plasmon resonance band to the red and increase its intensity. Importantly, the wavelength dependence of enhancement directly corresponds with the synchronous scattering, as shown in FIG. 8

Figure 10:
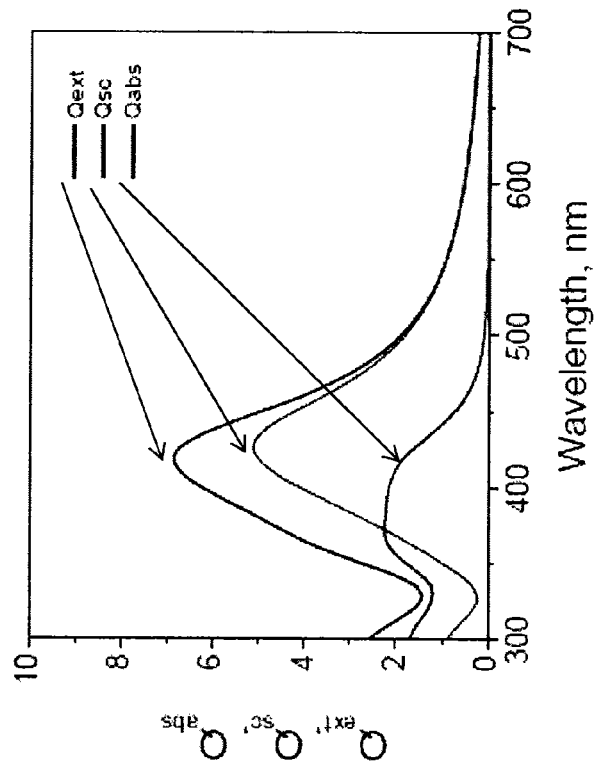
FIG. 10 shows the absorption and scattering components of the plasmon extinction spectra of the multilayers of nanoparticles of the present invention.
Figure 10:
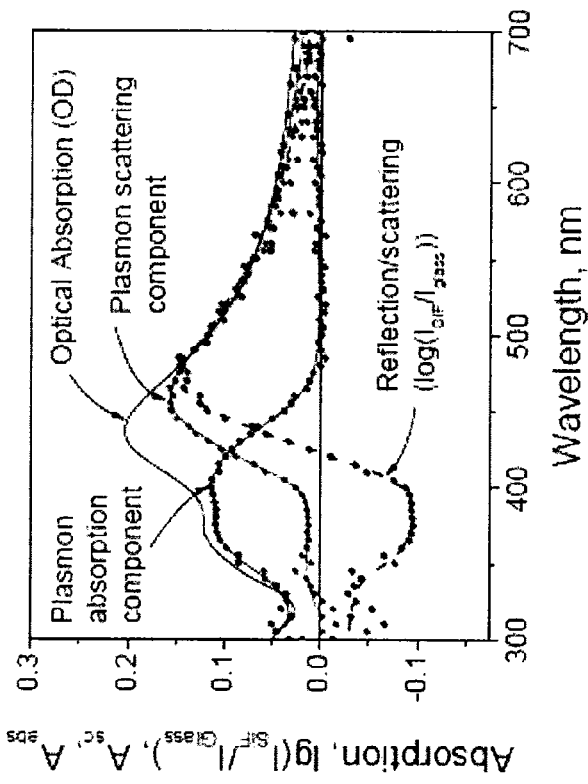
Figure 11:
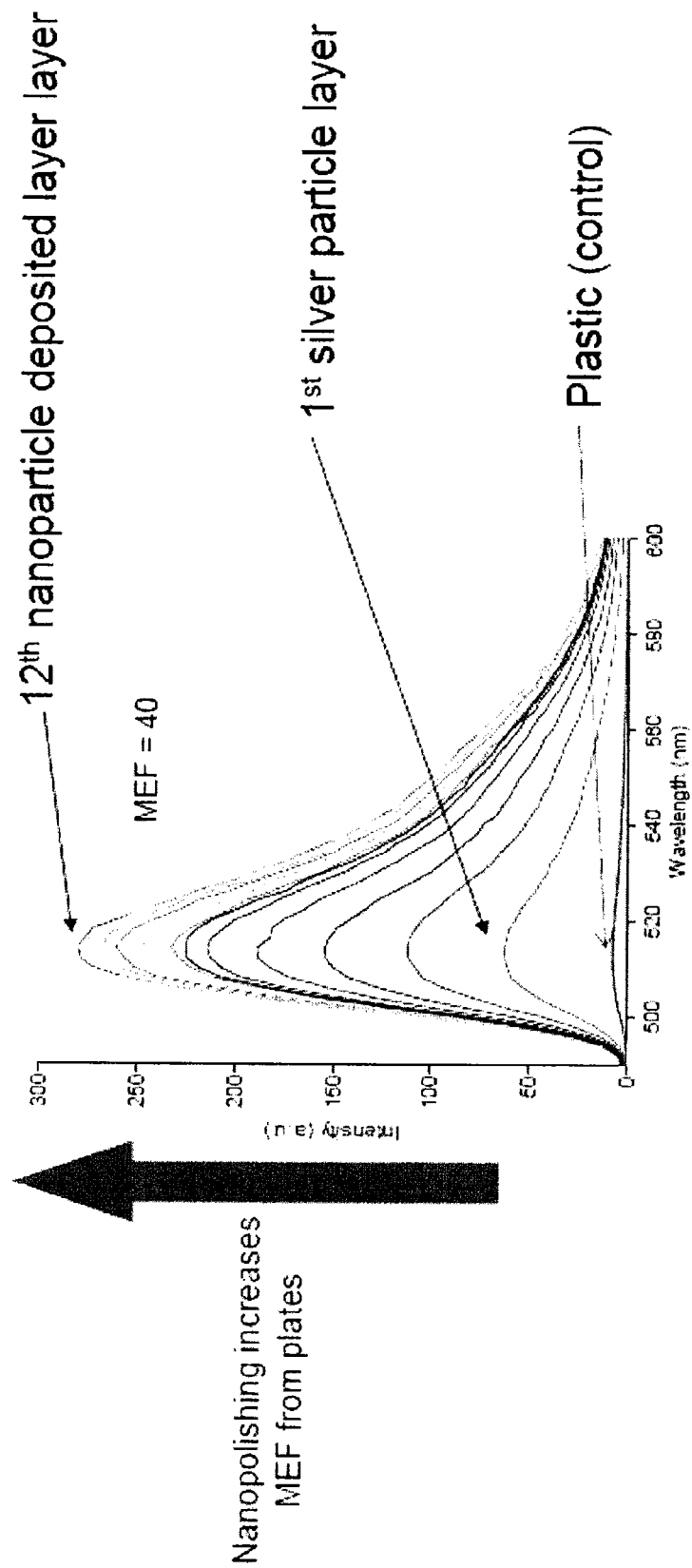
FIG. 11 shows the Metal-Enhanced Fluorescence (MEF) characterization of the plates with multilayers of nanoparticles of the present invention.
Figure 12:
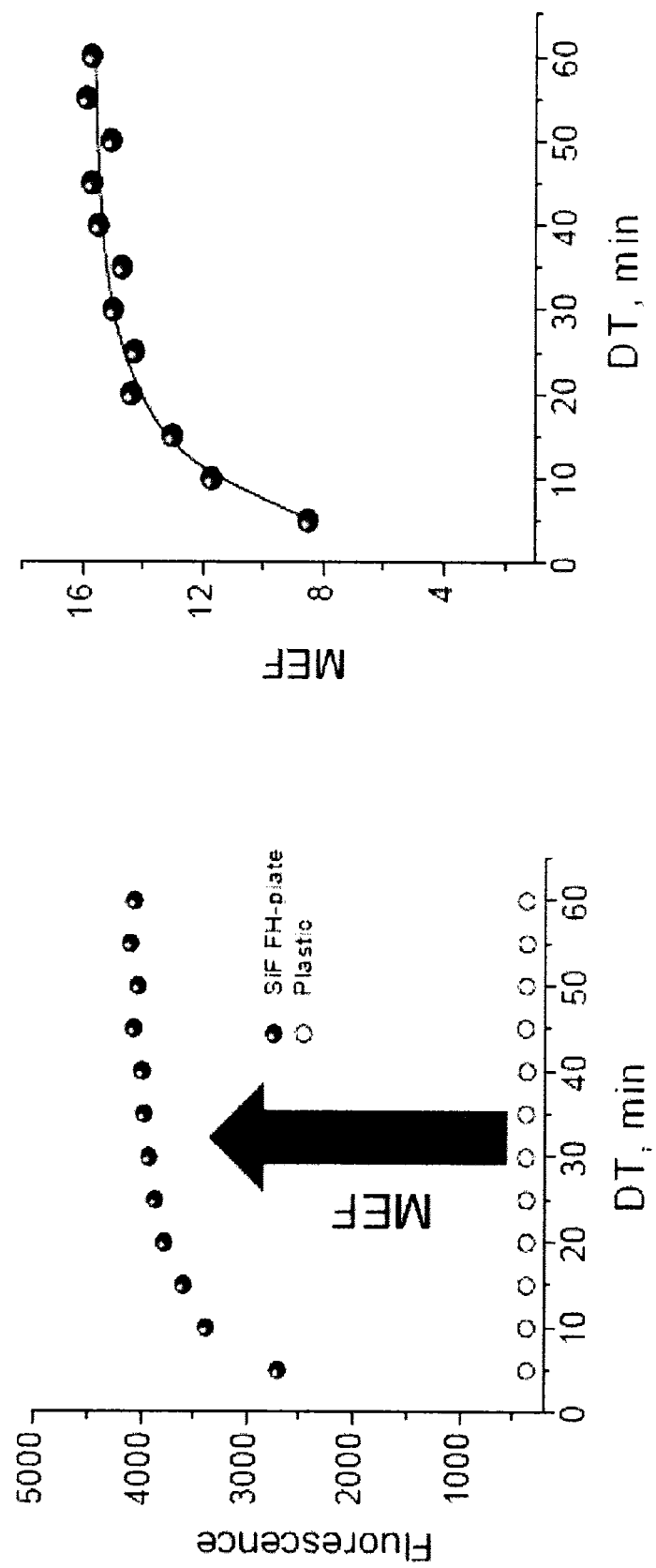
FIG. 12 shows the enhancement (MEF) of Fluorescein fluorescence in the plates of the present invention using a Spectra M5 Plate Reader.
Figure 13:
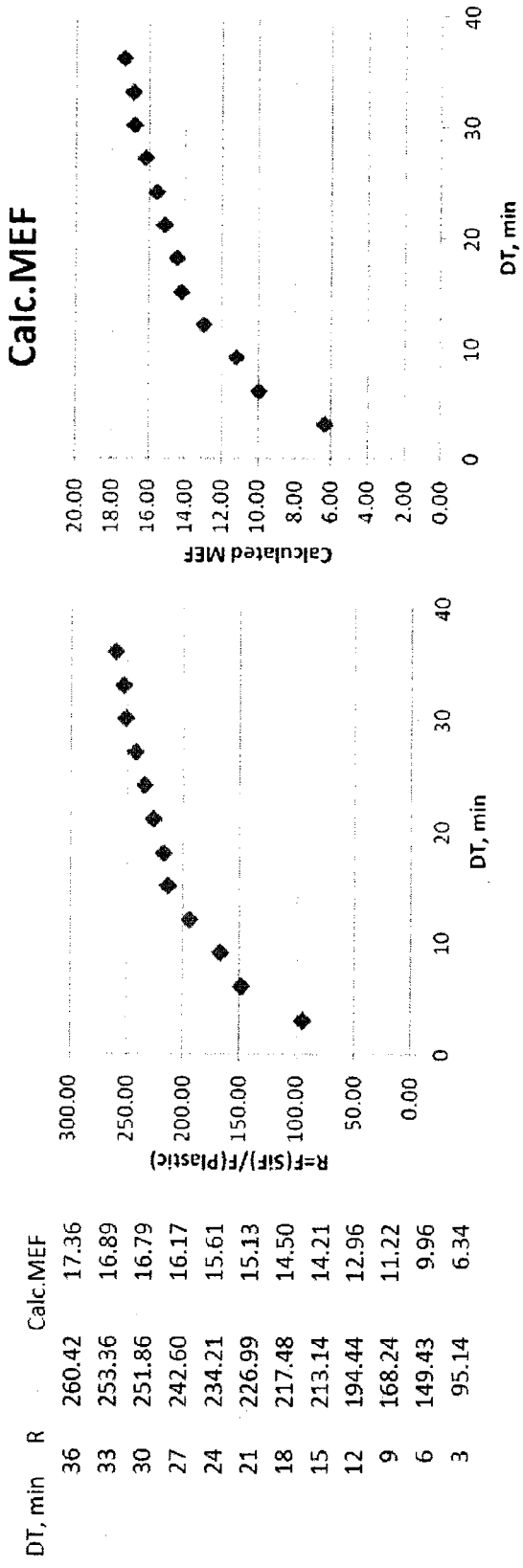
FIG. 13 shows that the synchronous scatter spectra is a predictor of MEF from the plates of the present invention.

FIG. 10 provides the analysis of the analysis of the absorption and scattering components of the plasmon extinction spectra of silver nanoparticles film surface on the plate wells using measured optical absorption and synchronous spectra. Deconvolution of the plasmon optical absorption spectra (OD) and plasmon reflection/scattering spectra on plasmon absorption ($A_{abs}$) and scattering ($A_{sc}$) components. (Right) Mie theory simulation of extinction, scattering and absorption components of the plasmon resonance band of the 50 nm silver nanoparticle (NP), $Q_{ext}$, $Q_{sc}$ and $Q_{abs}$, respectively. There is remarkable overlap between experiment and theory strongly suggesting that Plasmon scattering component of nanoparticles can be obtained by synchronous scatter measurements FIGS. 11 and 12 provide an overview of the metal enhanced fluorescence characterization of the multilayers of nanoparticles. Two separate plate readers were used to provide such data, the plate readers include very different collection optics. Notably, the Varian reader (FIG. 11) showed a 30-60 fold enhancement and the M5 Molecular Device showed about a 15 fold enhancement (FIG. 12) but this reduction is due to the optics of the instrument. As shown in FIG. 11, the 12$^{th}$ layer of nanoparticles shows a 40 fold increase of MEF. FIG. 13 shows the results of using the data from the M5 plate reader with an approximate enhancement fold of about 15-16 can be used to show that the synchronous scatter spectra is a predictor of MEF from the plates.

Figure 14:
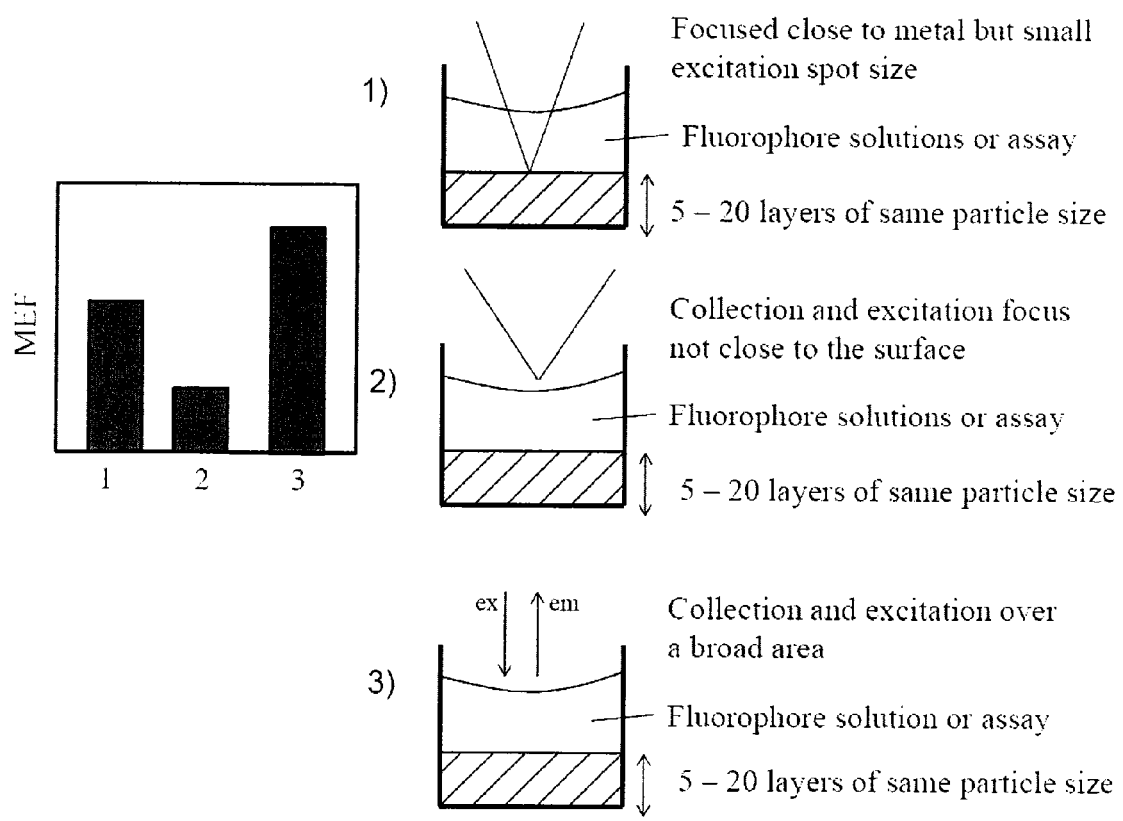
FIG. 14 shows the possible positions for collection and excitation focus on the multilayers of nanoparticles of the present invention.

FIG. 14 provides guidance for positioning of both the excitation and collection placement of optics for tunable sensitivity. Collection and excitation over a broad area provides the greatest MEF.

Figure 15:
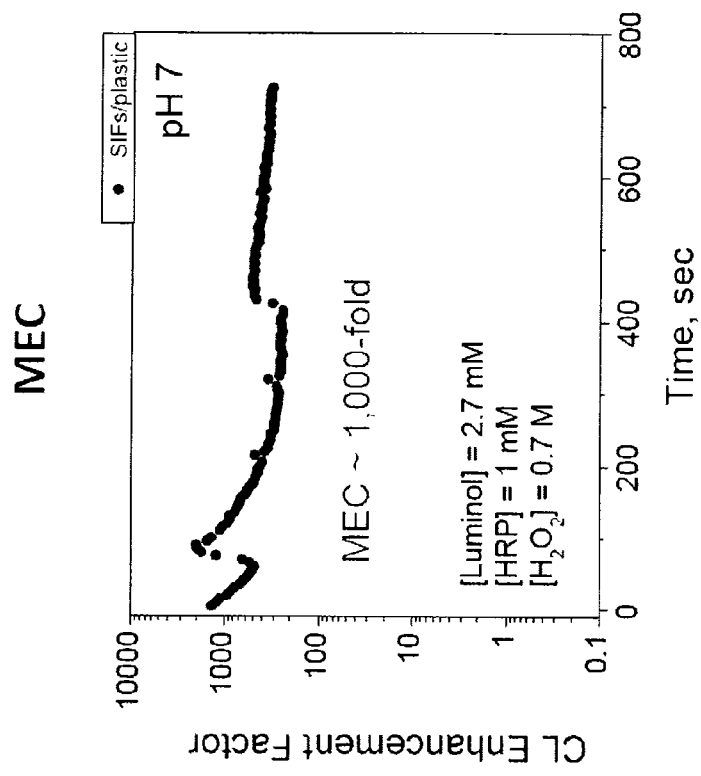
FIG. 15 shows that chemiluminscence can be enhanced 100 fold in the multilayers of nanoparticle plates of the present invention.
Figure 15:
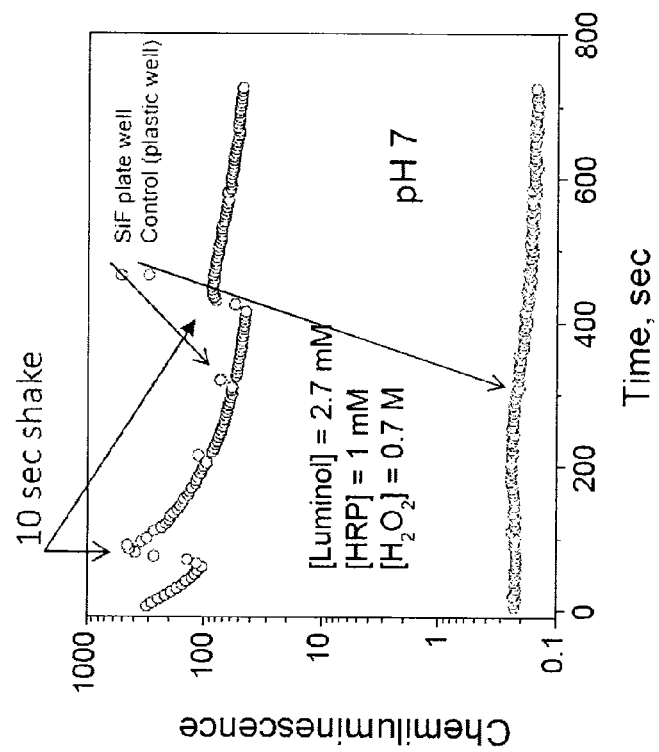
Figure 16:
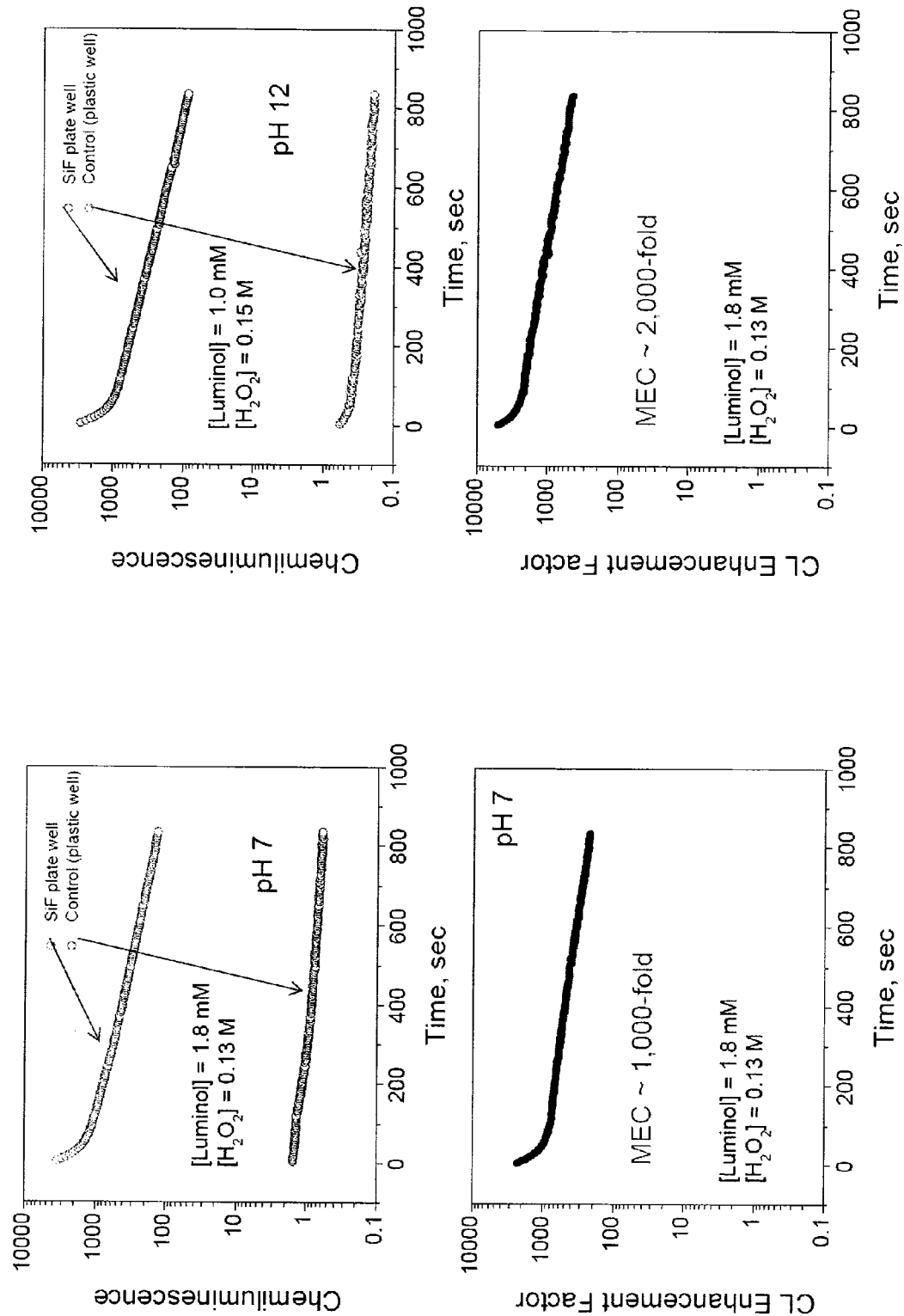
FIG. 16 shows that the enhanced chemiluminescence is pH dependent.

The multilayers of nanoparticles of the present invention are very effective for chemiluminescence reaction and assays using such molecules as signals. For example luminol is enhanced by coupling with the silver nanoparticles layer on assay plates. FIG. 15 show the effects of Luminol (L) and hydrogen peroxide (P) in the presence of Horseradish Peroxidase (HRP) as catalyst wherein the chemiluminescence was enhanced 1000 fold in the plates. FIG. 16 shows that the metal enhanced chemiluminescence is a function of pH. Up to 2000 fold enhancement is shown when the pH is raised to 12.

Figure 17:
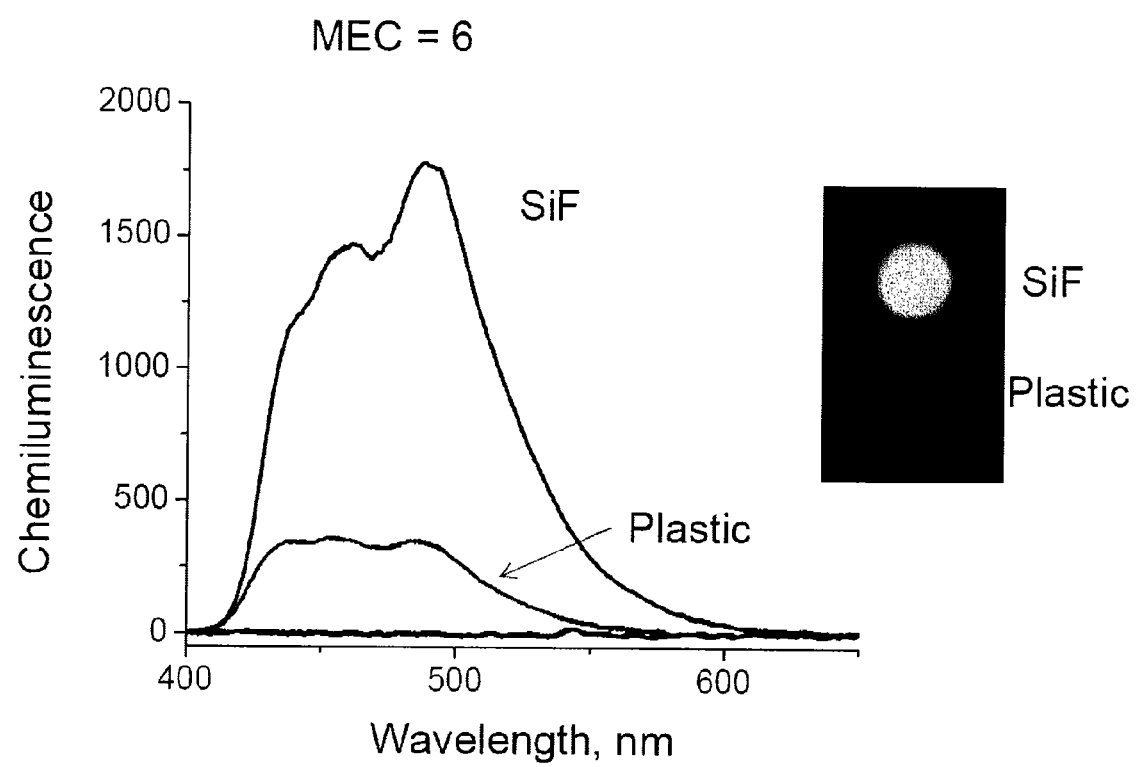
FIG. 17 shows the enhancement of bluestick solution chemiluminescence in the plate well coated with the multilayers of nanoparticles of the present invention.
Figure 18:
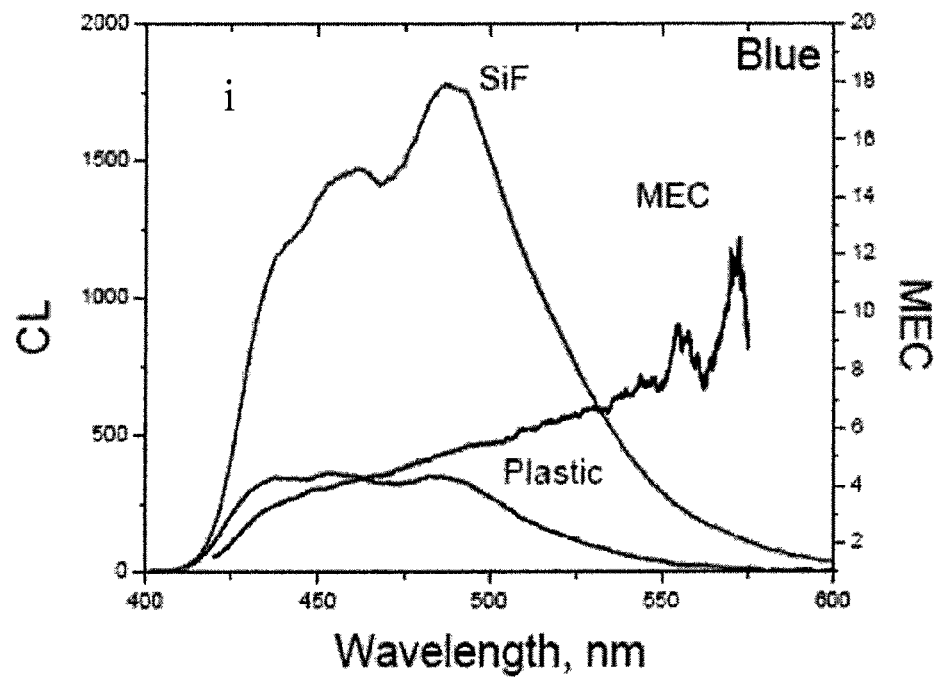
FIGS. 18 A-C show that the multilayers of nanoparticles of the present invention enhances glow stick chemiluminescence greater than 10 fold. A-Blue (i), Orange (ii); B-Yellow (iii), Pink (iv); C-Green (v), wells showing colors (iv).
Figure 18:
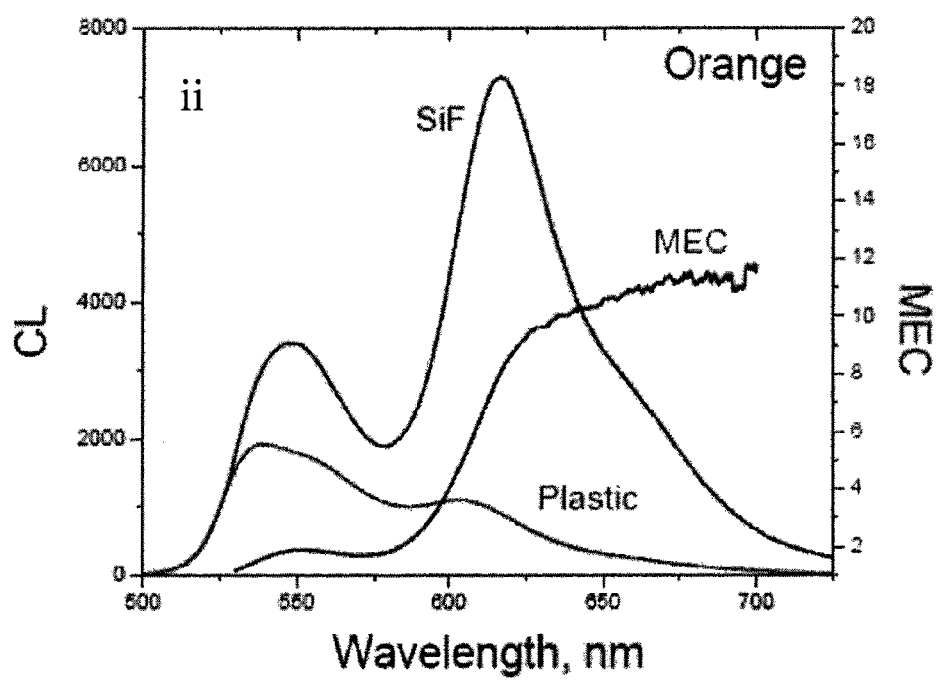
Figure 18:
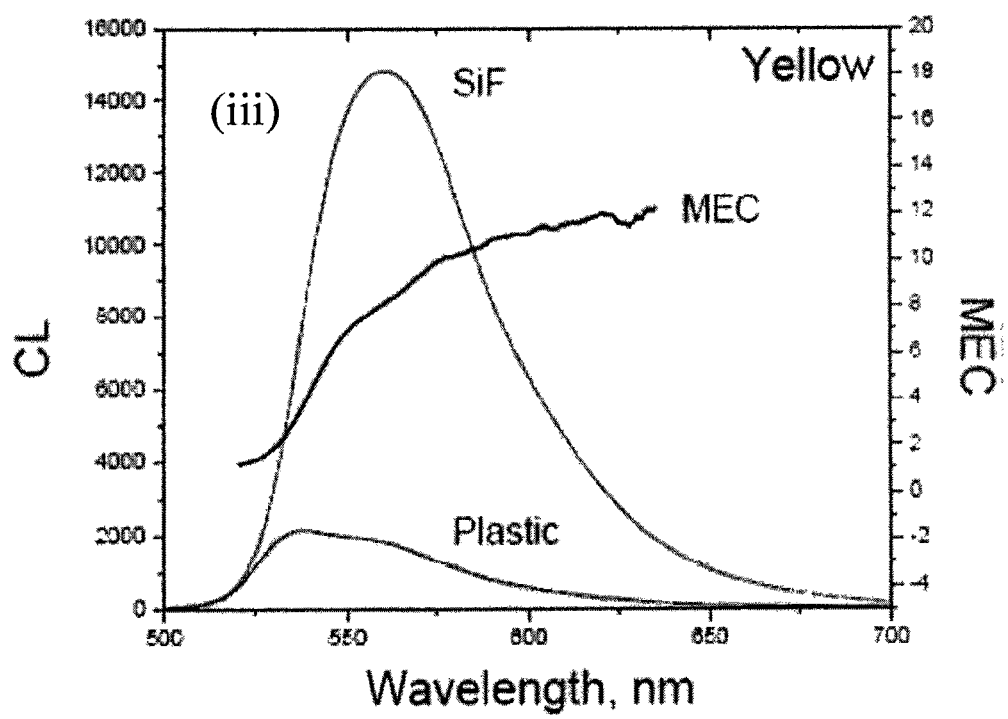
Figure 18:
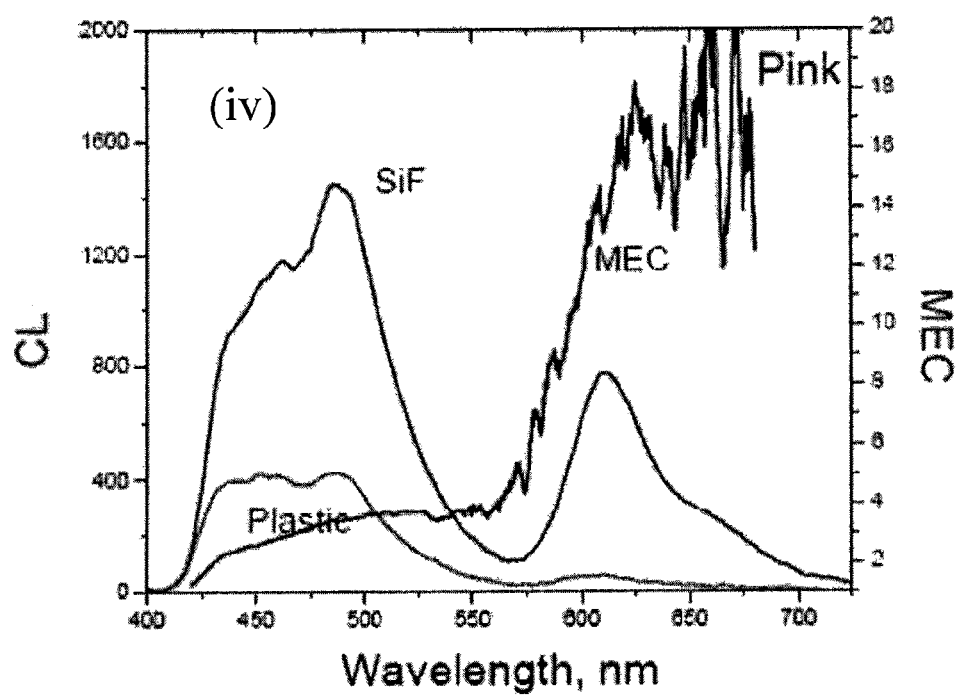
Figure 18C:
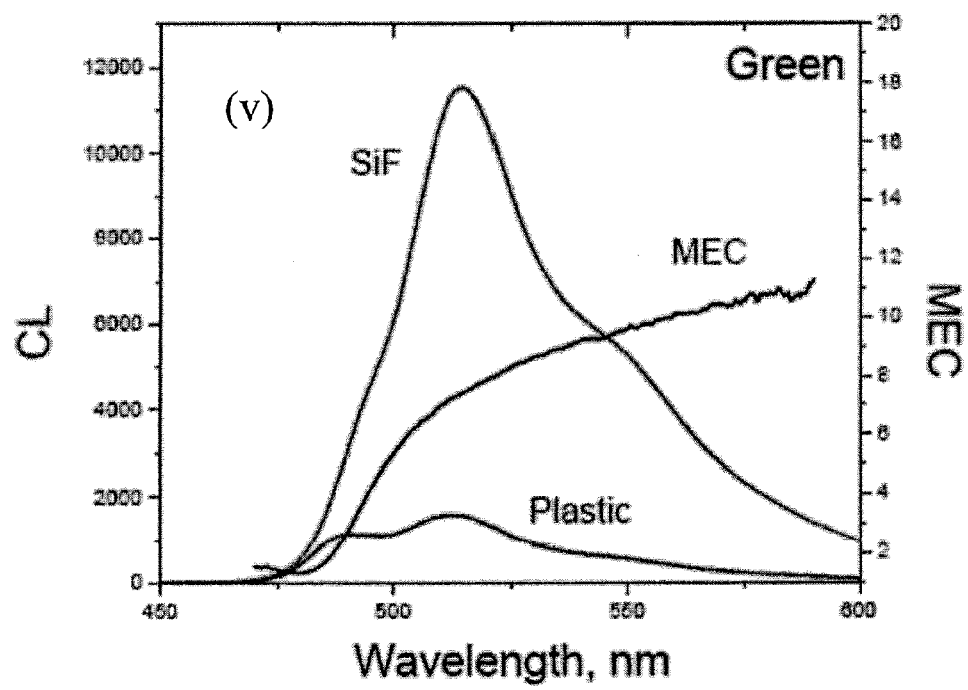
Figure 18C:
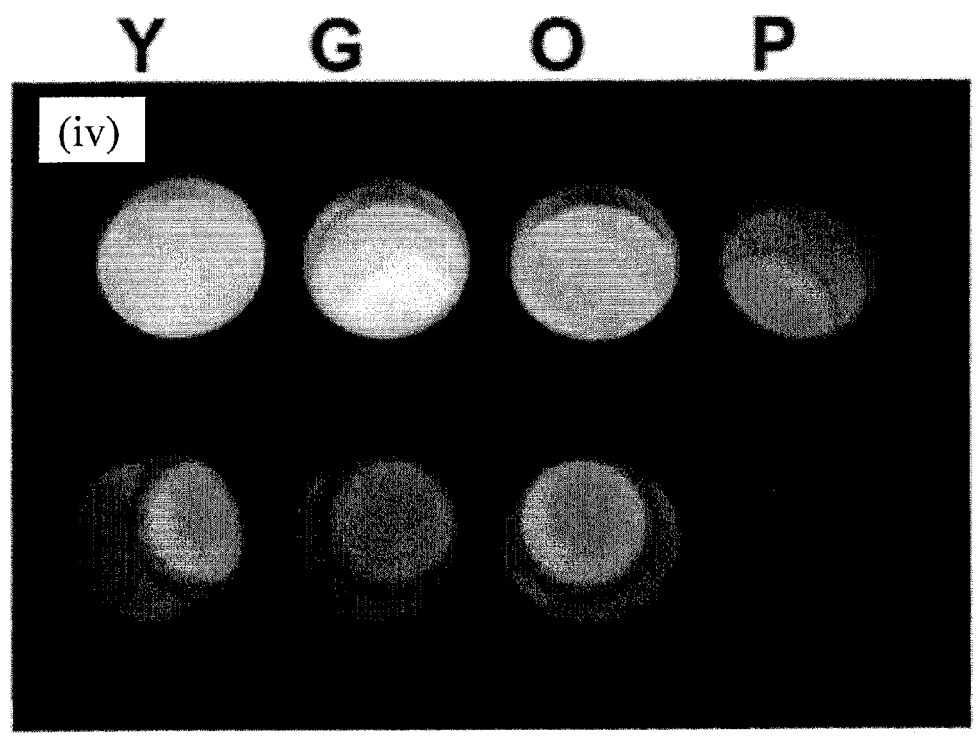

FIG. 17 shows the enhancement of chemiluminescence of a blue lightstick solution. Notably the enhancement is 6 fold relative to the plastic control. FIG. 18 provide for an interesting outcome, wherein the plates with the multilayers of nanoparticles enhances glow stick chemiluminescence >10-fold, but remarkably shows a wavelength dependence of enhancement, consistent with the synchronous scattering spectra of the multilayer nanoparticles wells.

Figure 19:
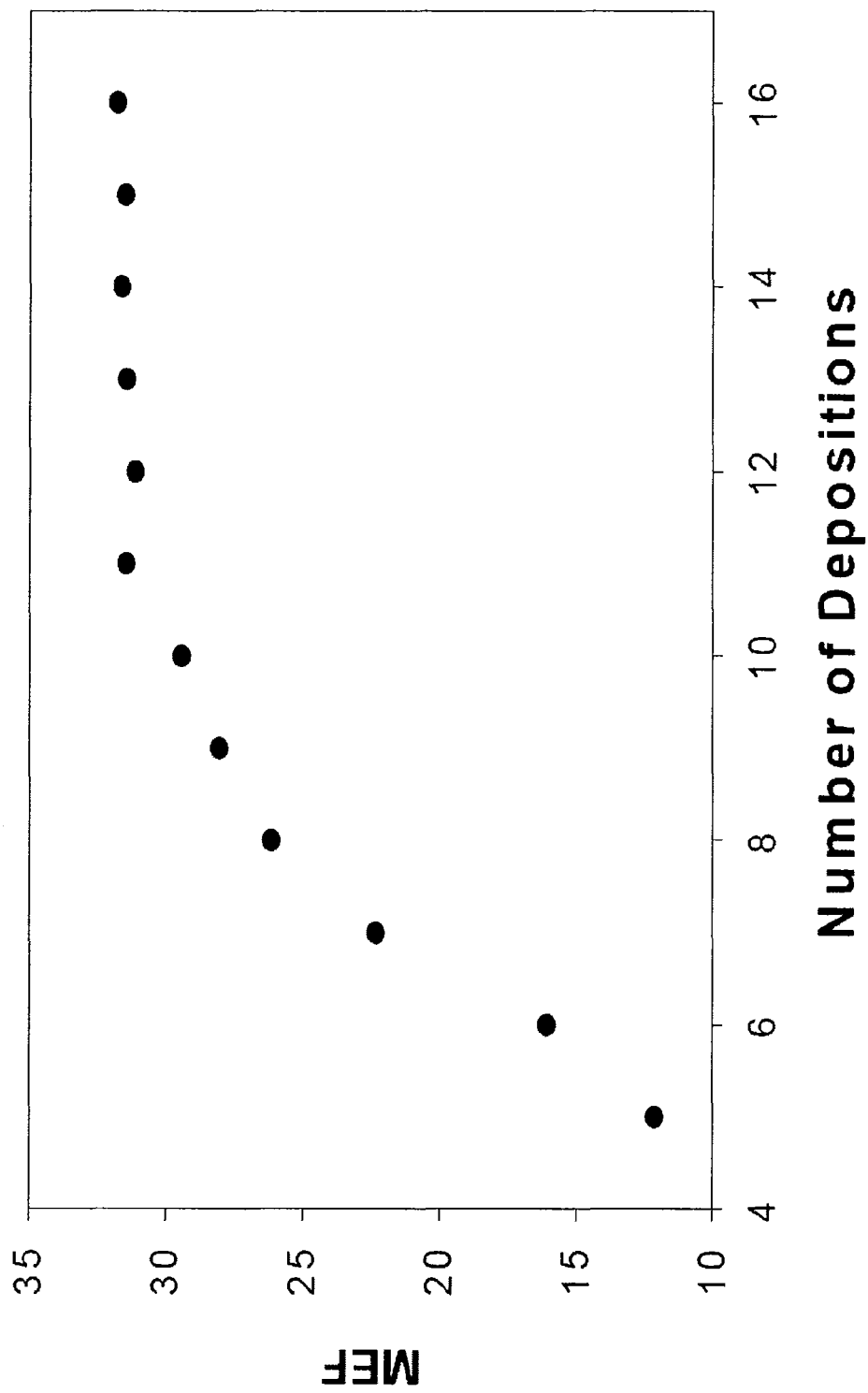
FIG. 19 shows the level of MEF of fluorescein versus the number of depositions.
Figure 20:
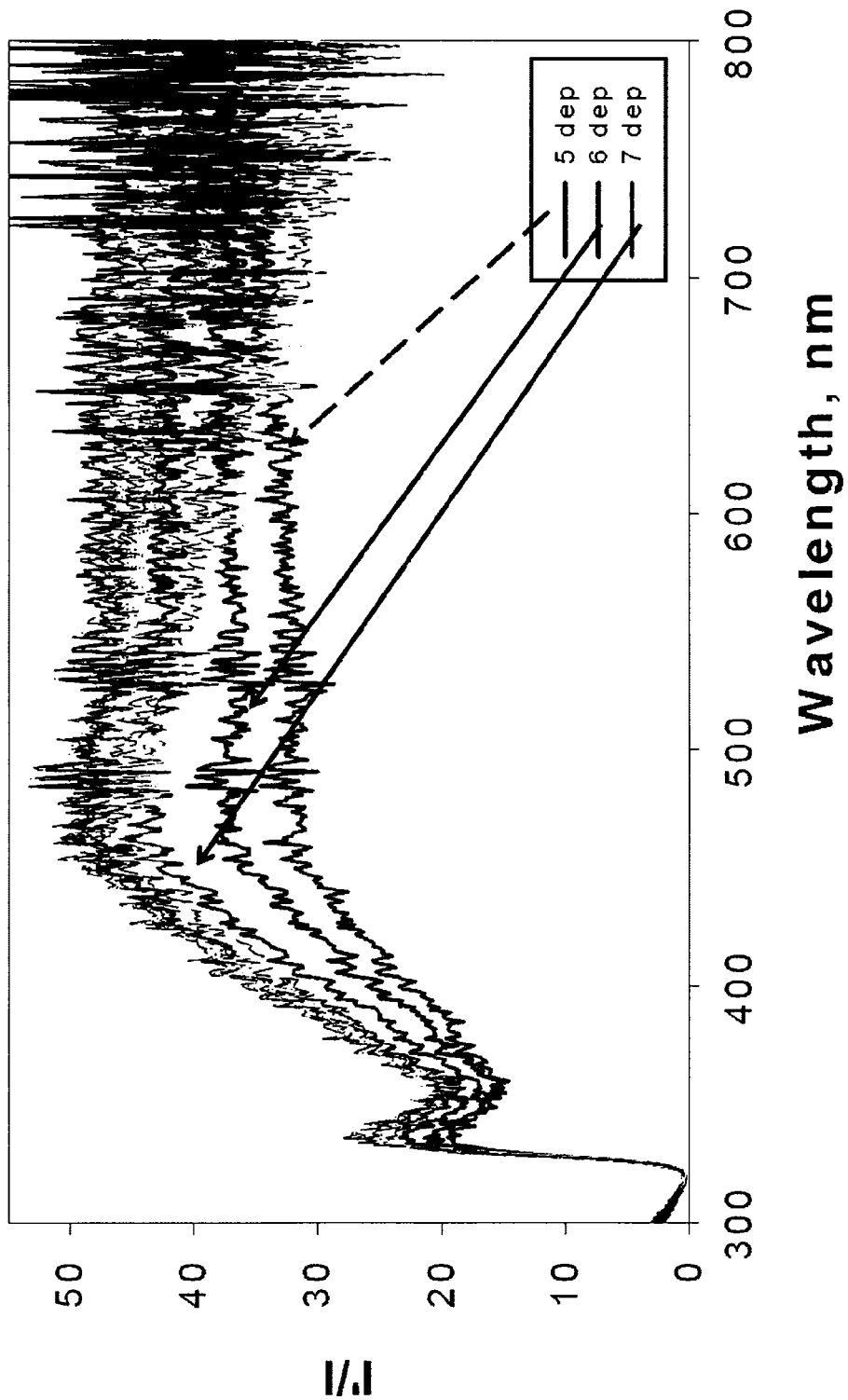
FIG. 20 shows the results from synchronous scattering spectra of the plates of the present invention with various number of depositions.

The present invention, having the multilayers of nanoparticles, shows an increased metal enhancement of the fluorophore fluorescein with each additional layer until a MEF is reached at about 12 depositions as shown in FIG. 19. FIG. 20 shows the synchronous scattering spectra of the multilayers of nanoparticles depending of the various numbers of depositions. This data shows the direct correlation of the number of depositions in the plates with the rising synchronous spectra values. Thus, the synchronous spectra is in reverse an analytical tool for determining both the magnitude and wavelength dependence of the MEF surfaces of the present invention.

Figure 21:
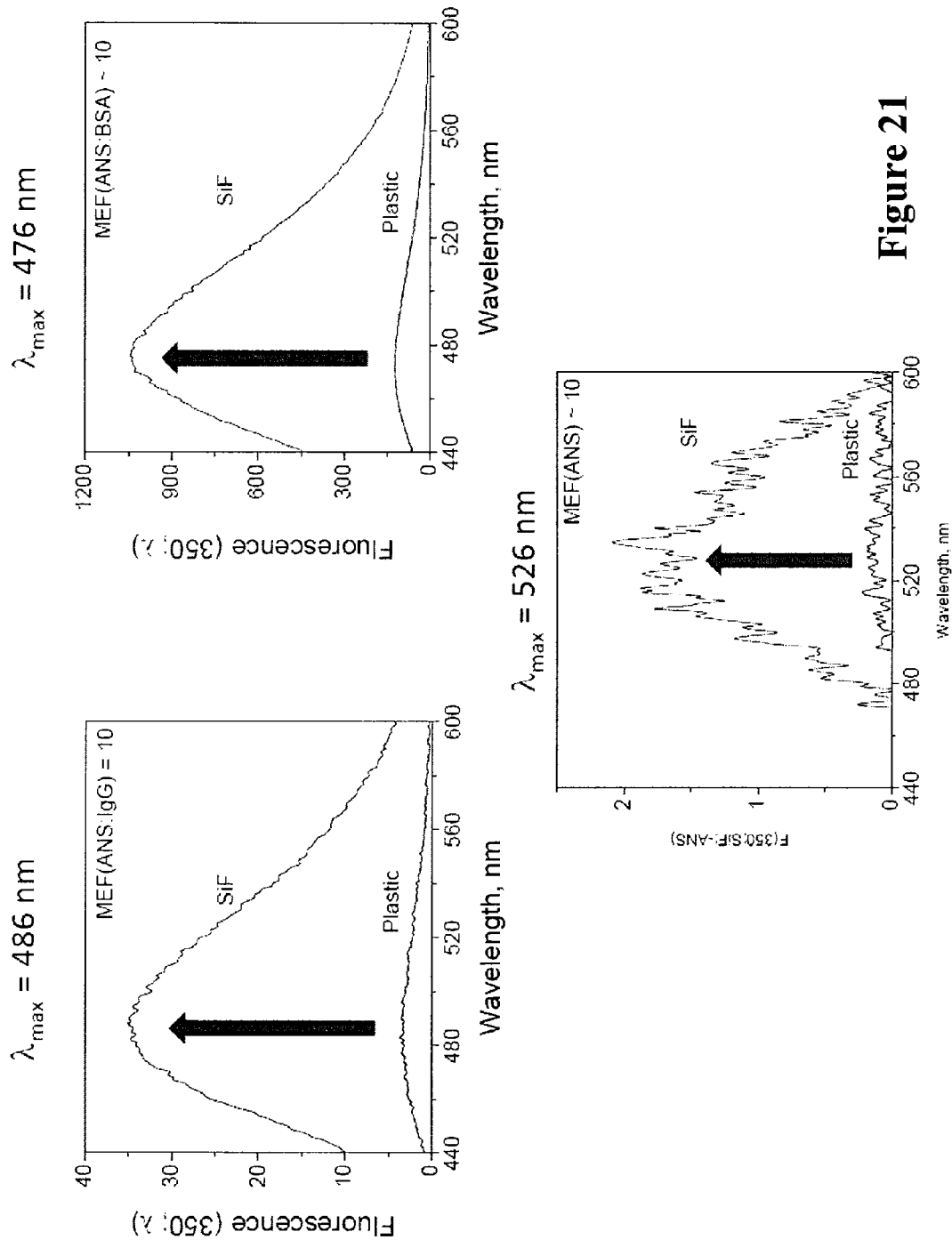
FIG. 21 shows the MEF of 1-anilino-8-aphthalene sulfonate (ANS) in complex with the IgG protein.
Figure 22:
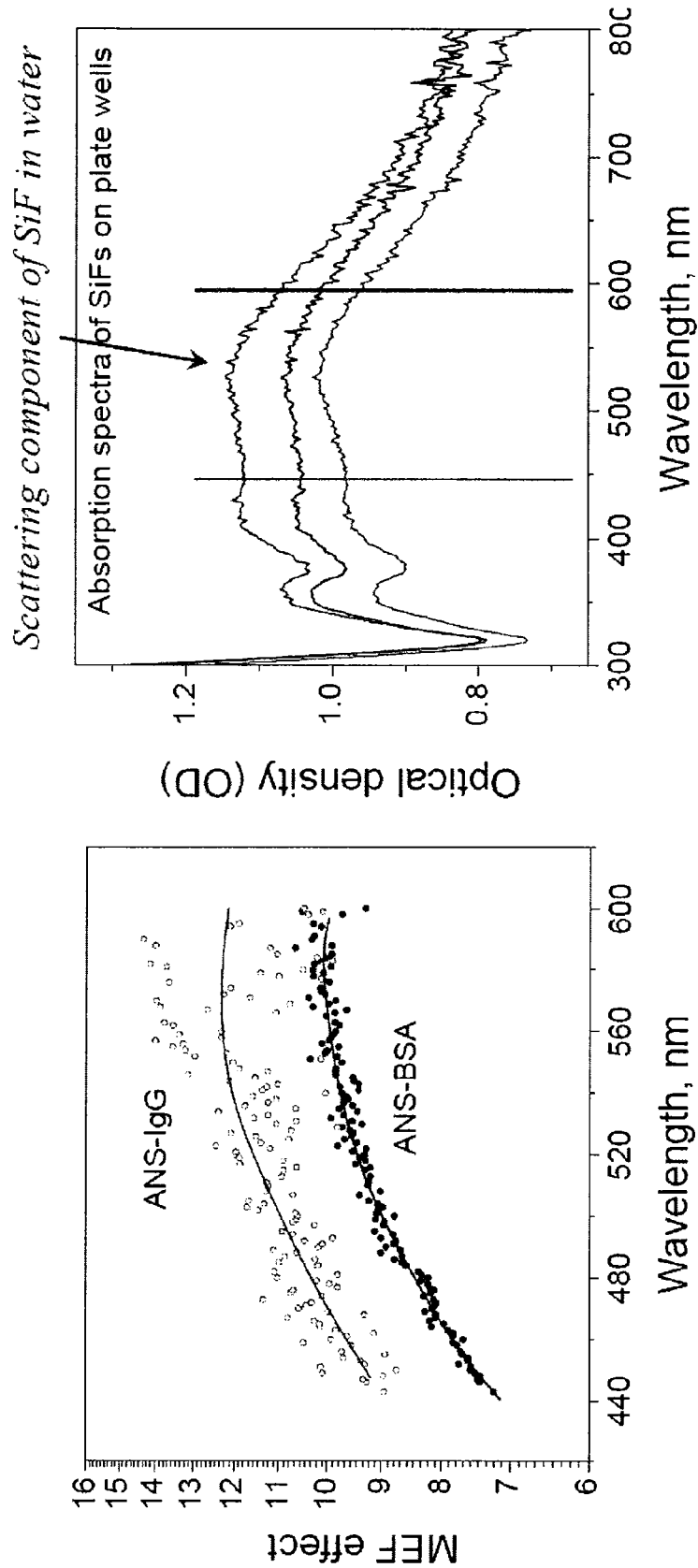
FIG. 22 shows the MEF of ANS depends on a wavelength of ANS emission.

In FIG. 21, the metal enhanced fluorescence of 1-anilino-8-naphtalenesulfonate (ANS) in a complex with an IgG protein shows the wavelength dependence of MEF from the multilayer of nanoparticles. It has been found that the MEF of ANS depends on a wavelength of ANS emissions. The dependence of MEF=f(wavelength) correlates with scattering component of the silver particles extinction spectra, as shown in FIG. 22.

Figure 23:
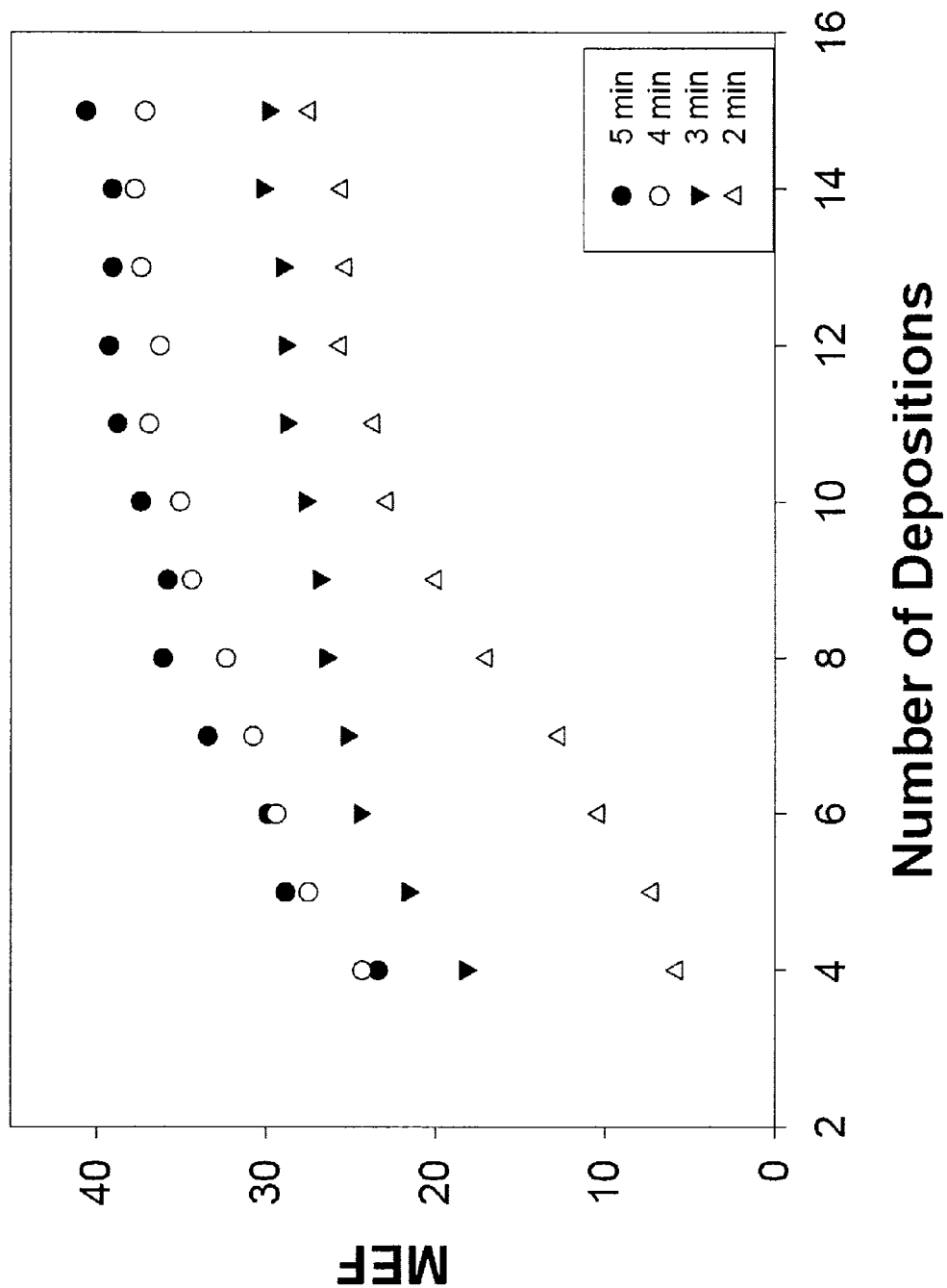
FIG. 23 shows the MEF of nanoparticles having a deposition time from 2 to 5 minutes using fresh silver containing solution.
Figure 24:
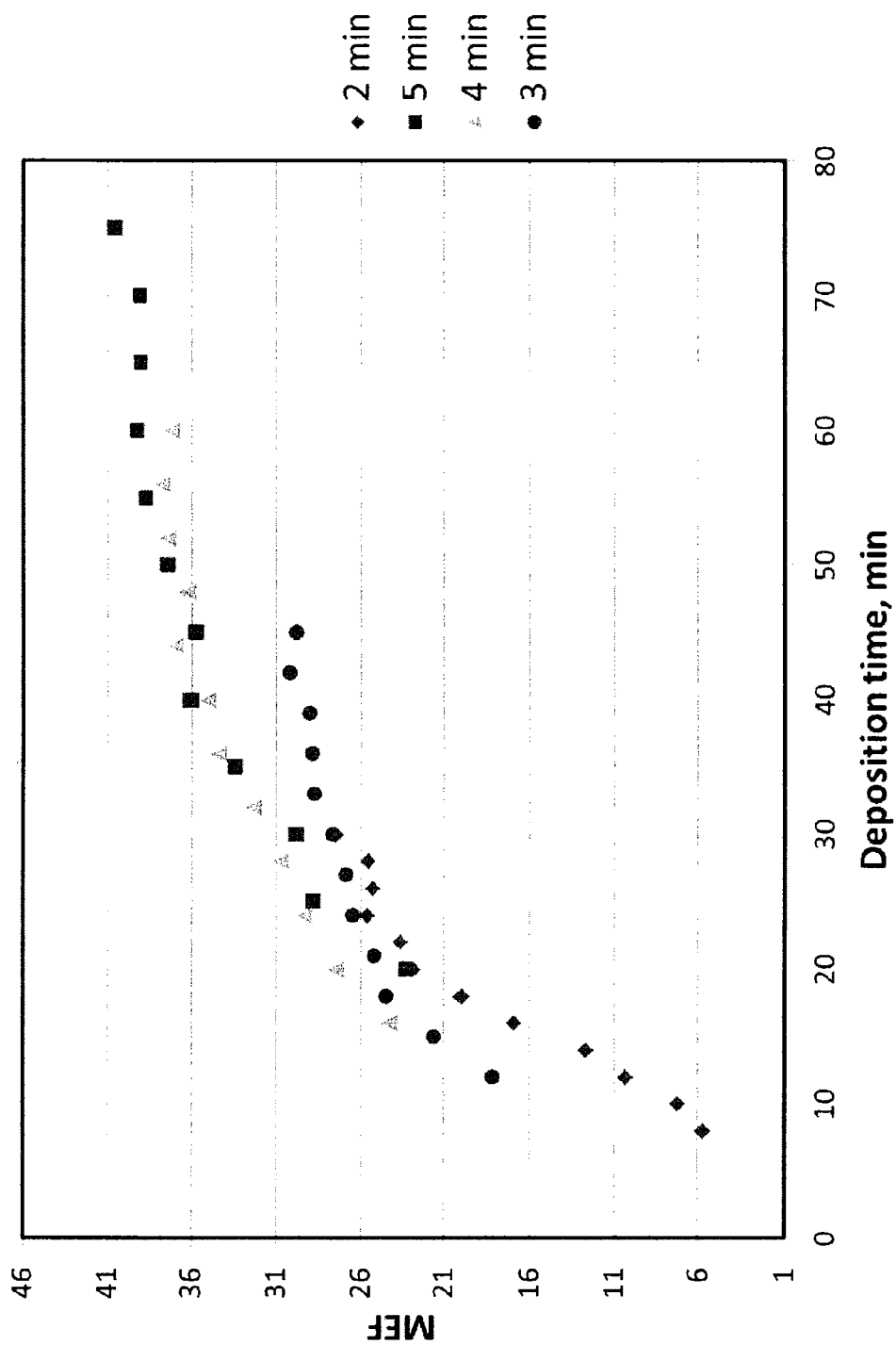
FIG. 24 shows the MEF of nanoparticles having a deposition time from 2 to 5 minutes using old silver containing solution
Figure 25:
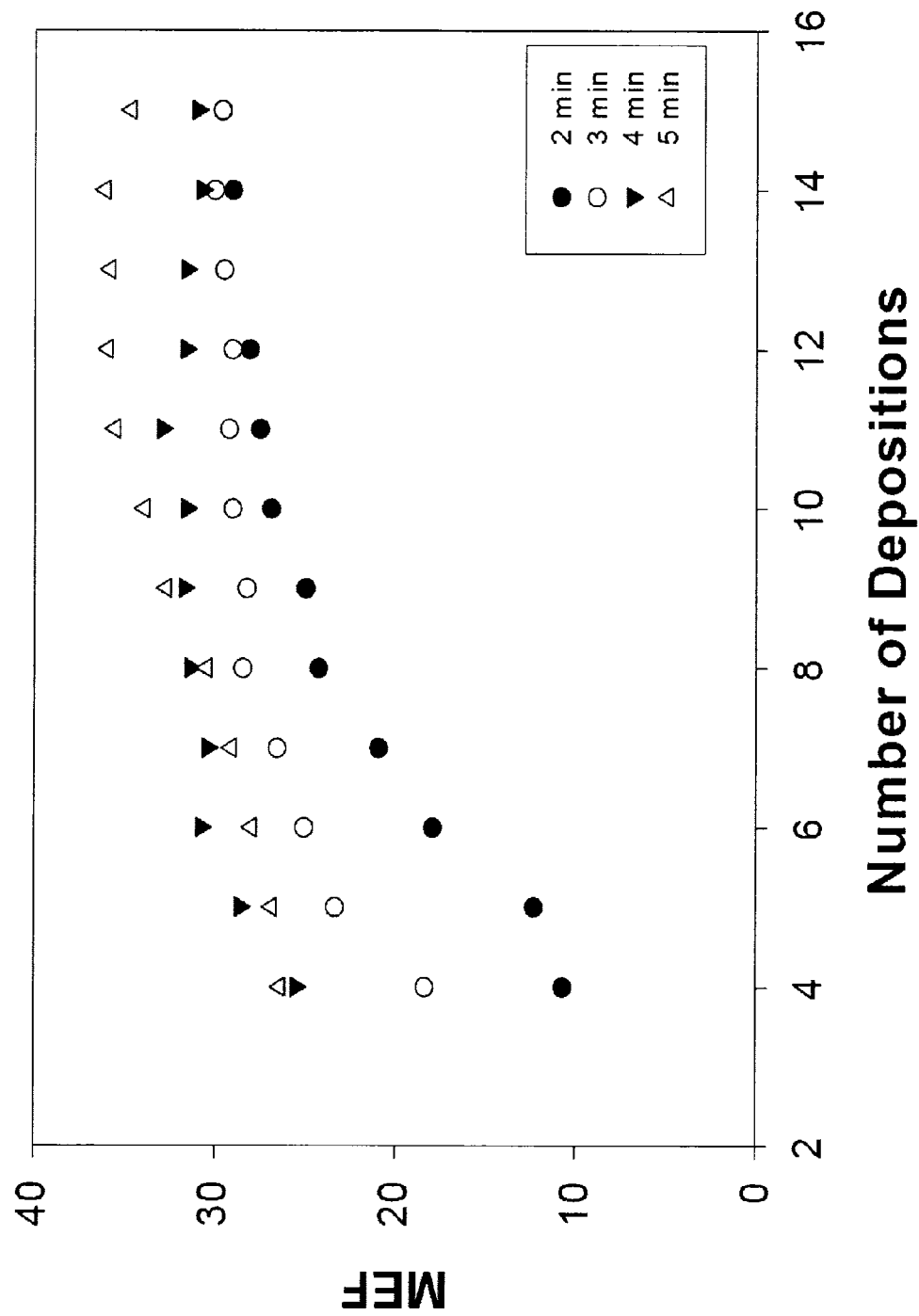
FIG. 25 shows a repeat of deposition with a fresh silver solution.
Figure 26:
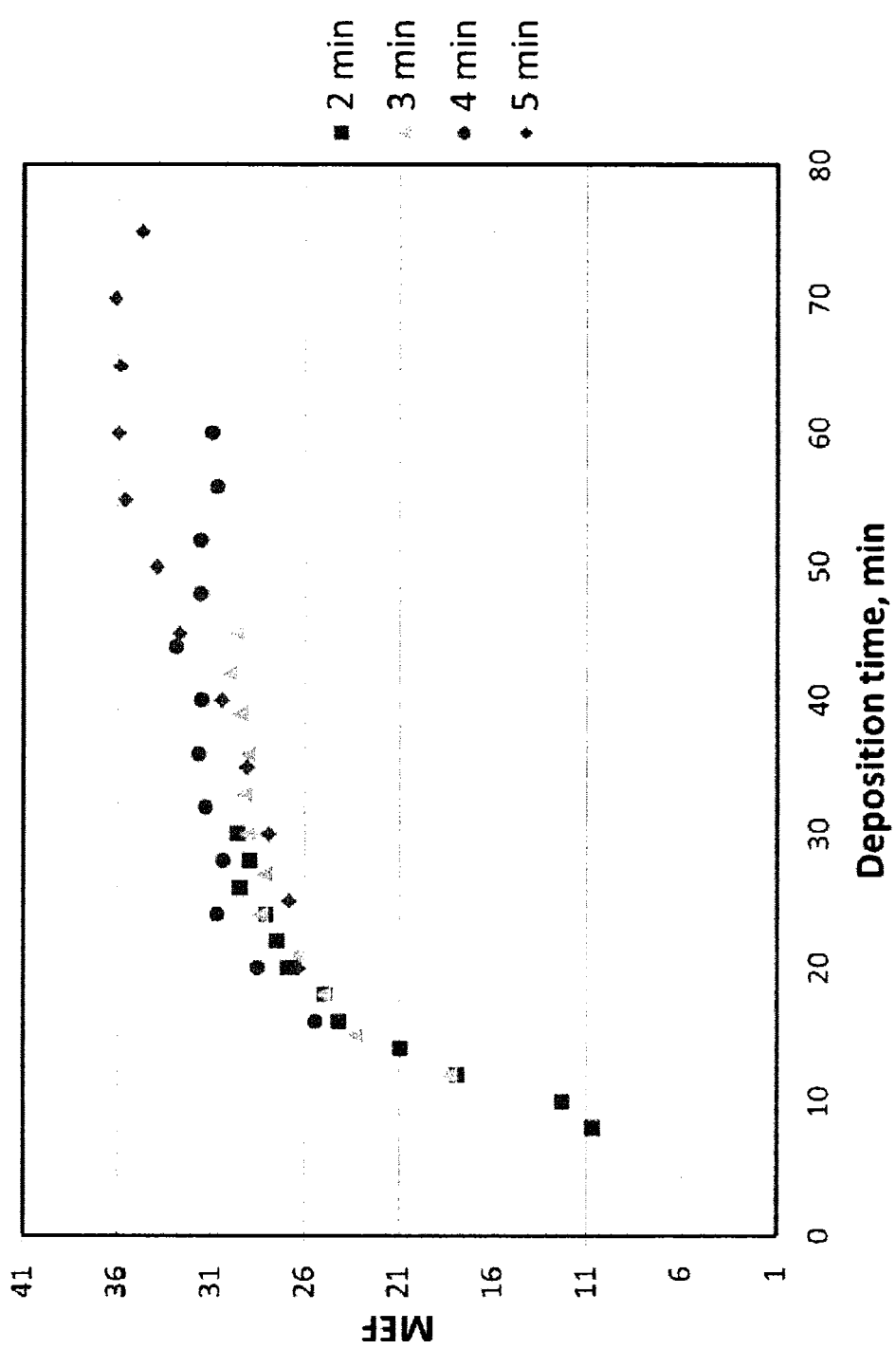
FIG. 26 shows a repeat of deposition with a fresh silver solution.

FIGS. 23 to 26 show results relating to coat thickness (layers of nanoparticles) and how time of deposition affects the enhancement factor for MEF. FIG. 23 shows that in individual well, as the incubation time is increased, that being the time the solution is left in the wells before being removed and a fresh solution is added, as well as the number of times this is repeated (number of depositions), the enhancement factor increases. FIG. 24 shows similar effect but an old stock solution of silver is used instead. Notably, the deposition time on the x-axis is simply the cumulative time of incubations. Both FIGS. 25 and 26 show results using a fresh silver solution. Clearly from the results, many depositions provide better enhancement and that longer deposition time within the wells generally gives better enhancement.

The fluorescence spectrum of Au-clusters (8- and 25-atom), which covers the spectral range 350 to 900 nm, is dramatically enhanced in the presence of plasmon supporting plate-well deposited nanoparticles. The wavelength-dependent Metal-Enhanced Fluorescence (MEF spectrum) correlates well with the plasmon specific scattering spectrum, i.e. the synchronous scatter spectrum of the silver surface of plate wells. The results suggest that the synchronous scatter spectra of plasmon enhancing substrates is a good indicator of the both the magnitude and wavelength-dependence of MEF.

The mechanisms of metal enhancement can be considered as due to at least two complementary effects: an enhanced absorption and an enhanced emission component. According to this interpretation the enhanced absorption in MEF is facilitated by the electric field generated by nanoparticles, the intensity and spectral distribution. Nanoparticle free oscillating electrons (plasmons) have specific absorption and scattering bands. The plasmon scattering component is sensitive to the size, shape and density of nanoparticles, and typically increases and broadens (red shift) with nanoparticle size. For silver nanoparticle films it has been found that the plasmon scattering spectra can be directly measured using the synchronous mode of spectral collection.

Materials and Methods

Chloroauric acid ($HAuCl_4$), ascorbic acid and bovine serum albumin (BSA) were purchased from Sigma (USA) and have been used without further purification.

Production of Fluorescent Au-clusters. Condensation of gold atoms into Au-clusters in the presence of protein (albumin) was undertaken according to (23) but using a few changes. In essence, an aqueous solution of chloroauric acid was added to the HSA protein solution in water, followed by the dropwise addition of a reducing agent, ascorbic acid, to trigger the formation of Au-clusters within the protein surface. The pH of the reaction was 11.7. In the original protocol the incubation time for obtaining fluorescent Au-clusters/protein was 6 hours at 37° C. In this modified protocol microwave irradiation of the reactive solution was employed for <30 sec in a microwave cavity (GE Compact Microwave Model: JES735BF, frequency 2.45 GHz, power 700 W). The microwave irradiation power was reduced to 20%, which corresponded to 140 W over the entire cavity. Microwave irradiation effectively accelerates the formation of Au-clusters within the protein structure.

Preparation of multilayers of nanoparticles silver-coated plates. Silver coating of Perkin Elmer plate wells was undertaken. In short, to prepare the silvering solution, 200 µl of sodium hydroxide solution (0.5% w/v) was added to 60 ml of $AgNO_3$ (0.83% w/v), the solution becomes brown and cloudy, after which 2 ml of ammonium hydroxide (30% solution) was added, or until the solution becomes clear. The solution was then cooled down on ice to 10° C. and, while stirring, 15 ml of fresh D-glucose solution (4.8% w/v) was added.

The silvering solution was then loaded into preheated (40° C.) plate wells for 2 min followed by cooling on ice for several minutes. The solution within the wells was changed several times, followed by continuous heating of the wells for several minutes. Finally, the plate was then washed several times with deionized water and dried in a stream of nitrogen gas.

Fluorescence measurements. Measurements of fluorescence excitation and emission spectra of the Au-protein samples were undertaken using a FluoroMax-4 spectrofluorometer (Horiba, USA).

Synchronous spectra measurements. Synchronous spectra of silver nanoparticle coated wells were measured using a Varian spectrofluorometer plate reader. In synchronous mode the instrument measures the intensity of light from wells at different wavelengths where the wavelength of excitation and emission are equal, i.e. λEx=λEm.

Figure 27:
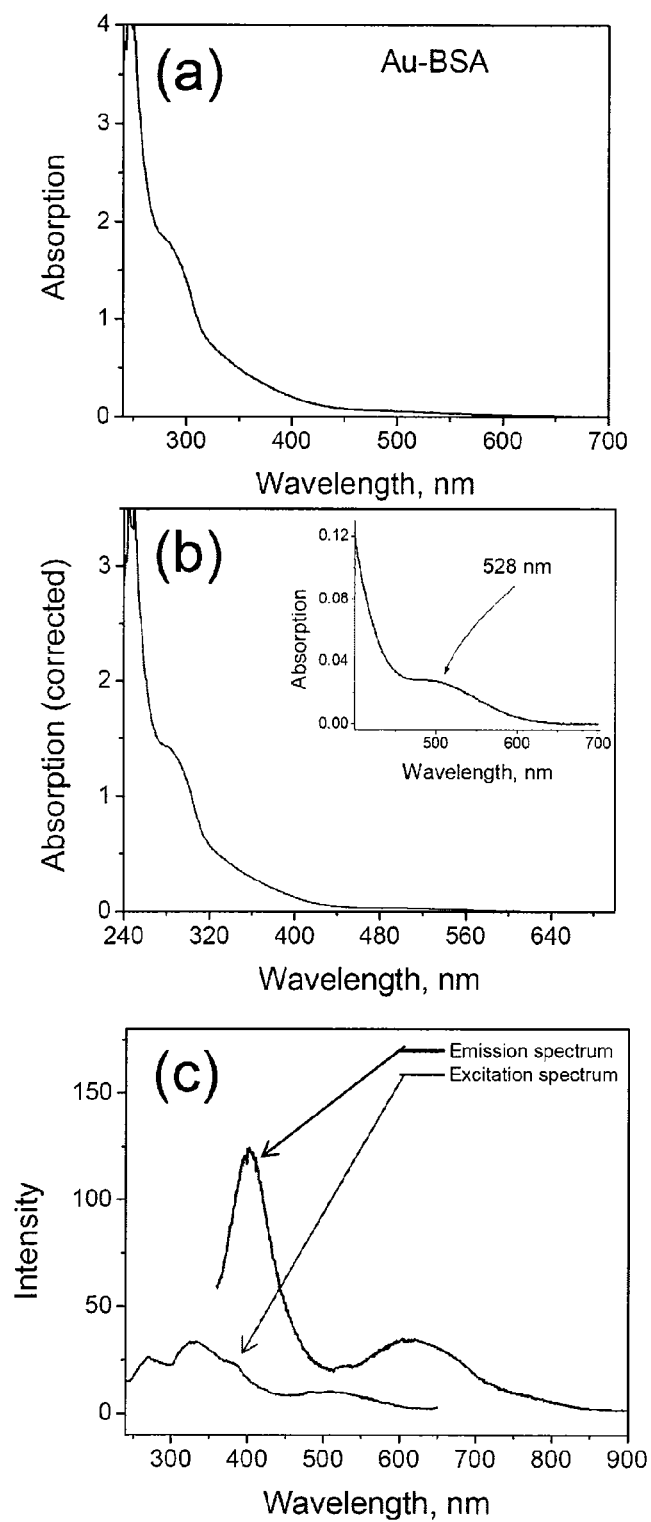
FIG. 27 shows (a) Absorption spectra of Au-Albumin solution. Sample was diluted 10-fold with PBS. (b) Corrected for scattering, the absorption spectrum of Au-Albumin solution. Insert: Enlarged absorption spectrum of Au-clusters shows specific absorption band at 528 nm. (c) Fluorescence and excitation spectra of Au-clusters (8- and 25-atoms). Fluorescence excitation spectrum was recorded using the 652 nm emission wavelength, i.e. maximum of Au-albumin fluorescence. Fluorescence spectra was recorded using the excitation wavelength at 340 nm.

Characterization of Au-clusters absorption and fluorescence. The absorption spectrum of the Au-cluster/protein sample is shown in FIG. 27. The spectrum consists of several overlapped spectra: Au-clusters absorption, absorption of the protein and some contribution of Raleigh scattering. The Raleigh scattering (RS) component of the absorption (optical density, OD) depends upon wavelength as OD=a/λn, where "a" and "n" are fitting parameters. The n parameter depends on the size of particles in solution (n=4 for particles smaller than the wavelength of the scattered light). In the logarithmic form it can be written as $$a \cdot \log(OD) = \log(a) - n \times \log(\lambda). \quad (1)$$

To determine the RS contribution we have fitted the spectrum, plotted in log(OD) vs. log(λ) coordinates, to equation (1). It is notable that the fitted n parameter is n=4, which suggests that particles, responsible for the light scattering, are small as compared to the excitation wavelength. The obtained scattering function, Equation (1), was subtracted from the original spectrum (FIG. 27a). The result is shown in FIG. 27b. FIG. 27b (insert) shows that the long-wavelength absorption band has a maximum at around 528 nm, which is attributed to the absorption of condensed Au-clusters. Relatively large gold nanoparticles (size >5 nm), which are not fluorescent, are characterized by a plasmon resonance band positioned at about 650 nm (24).

The Au-clusters are readily characterized by broad fluorescence and excitation spectra (FIG. 27c) over the wavelength range 350-900 nm. The fluorescence spectrum consists mostly of two components: blue and red fluorescence, which is known to correspond to the emission of both 8- and 25-atom Au-clusters, respectively.

Figure 28:
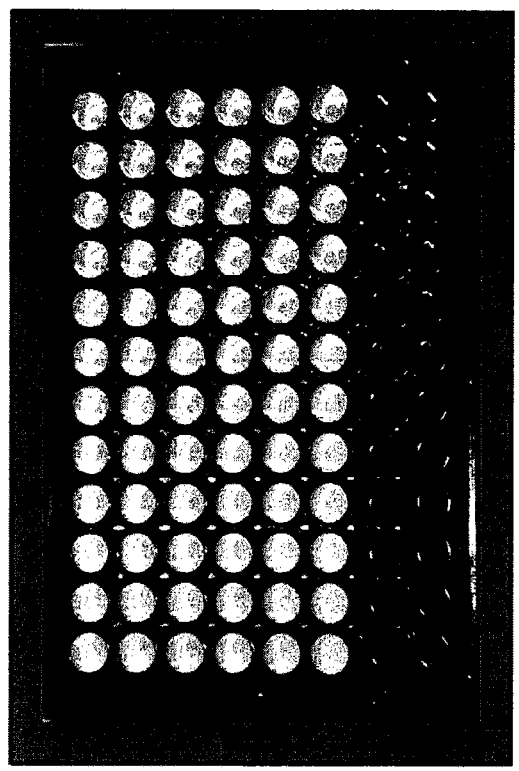
FIG. 28 shows (Left) Fluorescence and excitation spectra of Au-clusters from plates comprising multilayers of nanoparticles and control plastic wells. (Right) Real-color photograph of the a 96-well plate comprising multilayers of discrete nanoparticles, showing both the silvered and non-silvered (control sample) wells.
Figure 28:
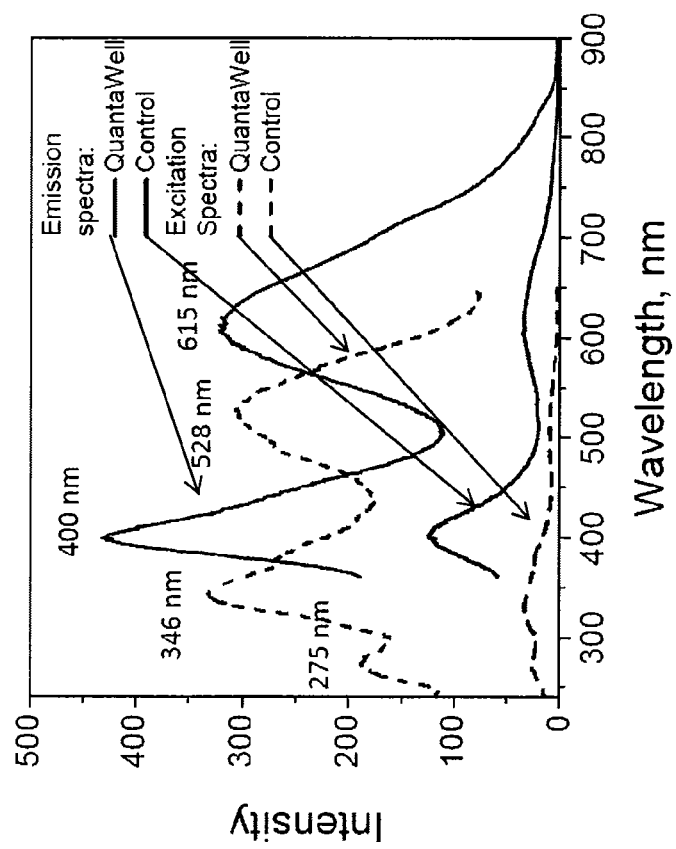

Metal-Enhanced Fluorescence of Au-clusters. The fluorescence of Au-clusters is dramatically enhanced in multilayer nanoparticle silver coated plate wells. FIG. 28 (left) shows fluorescence and excitation spectra of an Au-cluster/protein solution recorded from silver coated and uncoated control plastic wells, FIG. 28 (right). In the silvered wells both the fluorescence and excitation spectra show a large increase in intensity, relative to the control. The maximal observed MEF of Au-NCs is about MEF=40-50 fold.

In spectral terms, the fluorescent Au-clusters behave as classical fluorophores. They absorb and emit light, showing discrete electronic states and, accordingly, have dipoles in both the ground and excited state. Consequently, the origin/mechanism of the MEF effect shown in FIG. 28 could explain an enhancement of the Au-cluster fluorescence, in essence, by a coupling of the electronic system of a gold cluster with the induced surface plasmons of silver nanoparticles.

Figure 29:
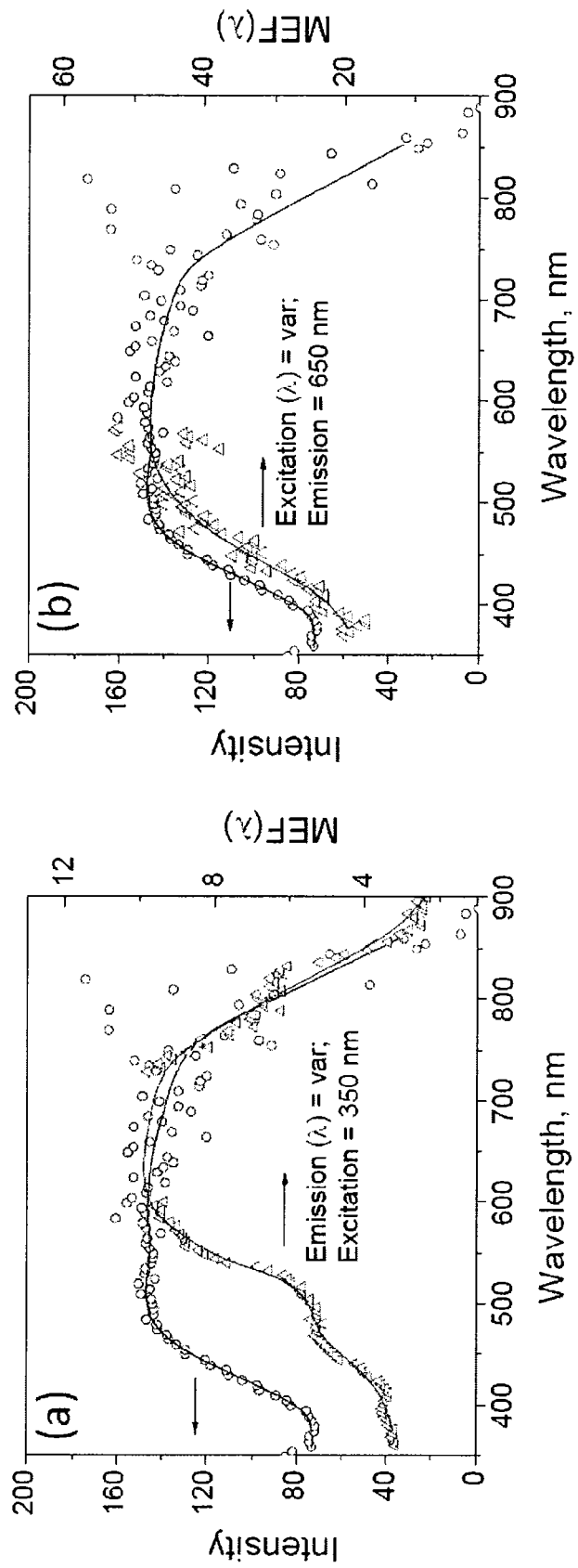
FIG. 29 shows superposition of the MEF effect and the synchronous reflection/scattering spectrum from plate wells comprising multilayers of discrete nanoparticles of the present invention. MEF($\lambda$) functions: (a) calculated as a ratio of fluorescence spectrum of Au-protein from plate wells as compared to the control spectrum from an uncoated plastic well (fluorescence excitation was at 350 nm); (b) calculated as a ratio of fluorescence excitation spectra of Au-BSA from plate wells to the control excitation spectrum from plastic wells (fluorescence was recorded at 650 nm).

The magnitude of the observed MEF depends on both the wavelength of excitation and emission as shown in FIG. 29. MEF is low (MEF=2-4) in the UV spectral range (<400 nm), reaches maximum value (MEF=50) in the visible range and is lower again down to MEF=2 in the near-infrared spectral area (>750 nm).

Figure 30:
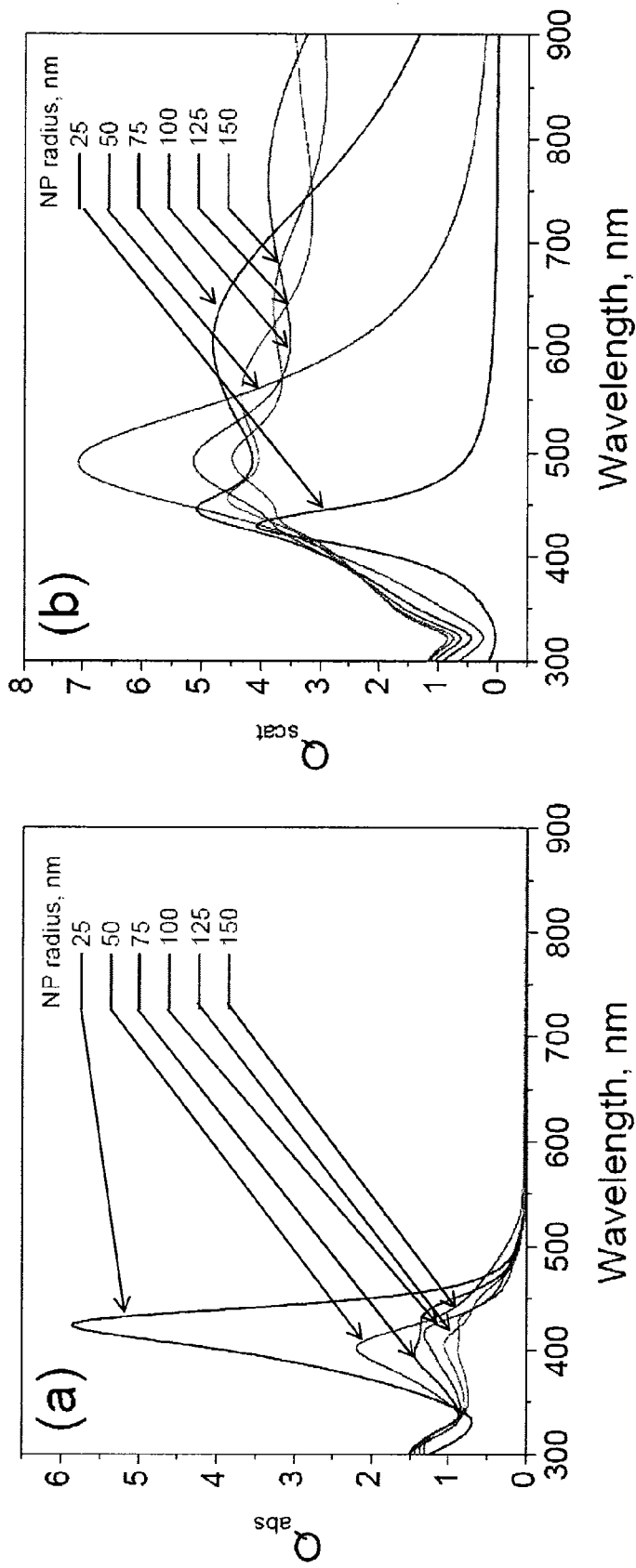
FIG. 30 shows Mie calculations of the absorption (a) and scattering (b) components of the extinction spectra of silver nanoparticle. The radius of the nanoparticles changes from 25 nm to 150 nm in the simulations.

Plasmon scattering from the silver surface: synchronous spectral analysis. To understand the wavelength dependence of enhancement further, the plasmon scattering spectrum was measured from the multilayer nanoparticle silvered surface and it was compared with the observed MEF spectrum. Silver particles, deposited on different surfaces (glass, quartz, various plastics), have different geometries: size, shape, density and, consequently, it is hard to simulate accurately their optical properties. Nevertheless, one can determine the general spectral properties of metal particles and their change with size. FIG. 30(a) and (b) shows theoretical Mie calculations of both the absorption and scattering spectra for different size silver nanoparticles. Absorption spectra are typically narrow and their spectral position (≈400 nm) does not change significantly, while the scattering spectrum is very sensitive to the size of the nanoparticles and becoming broad and shifting to the red when the NP size is >25 nm. For 75 nm diameter particles the scattering spectrum is quite similar to the MEF spectrum (FIG. 29), i.e. covers a wavelength range from 450 to 750 nm. Subsequently, it is postulated that the scattering component of a nanoparticle extinction spectrum can influence and modulate MEF in the broad VIS-NIR spectral region, and that this wavelength dependence can be determined from either i) simulations or ii) measuring the synchronous scattering spectrum, as described below.

The multilayer nanoparticles plate well of the present invention were specially designed to achieve a large MEF effect over a broad spectral range and such technique has been called the nanopolishing. The surface contains silver nanoparticles arranged on the surface in a specific multilayer manner. To characterize experimentally the spectral distribution of the plasmon scattering intensity the synchronous spectra from the silvered surface (FIG. 29) has been recorded. In a synchronous mode, the wavelength of excitation and emission are scanned simultaneously, which results in recording the reflection/scattering characteristic of the surface, i.e. it describes the nanoparticles' extinction spectrum. The maximal magnitude of reflection/scattering is in the spectral range of 450-750 nm and decreases at the wavelengths <450 nm and >750 nm. It is notable that the MEF spectrum coincides very well with the synchronous scattering spectrum (FIG. 29), suggesting that synchronous scatter measurements are a good predictive tool for the wavelength dependence of MEF. It is also interesting that in the 400-600 nm range, the magnitude of the MEF spectrum, estimated using the emission spectra (FIG. 29a), is lower than that calculated from the fluorescence excitation spectrum (FIG. 29b). It is theorized that this difference is a consequence of the re-absorption or energy migration between fluorescent nanoparticles which are sited within one protein molecule. The shape of the MEF spectrum in the visible region, shown in FIG. 29(a), is a mirror-like image of Au-NCs absorption. As it can be seen from FIG. 28 (left), the intense absorption band of Au(25) is positioned entirely in this spectral region, having a maximum at about 528 nm. In the case of MEF calculated using the fluorescence excitation spectra (fluorescence registration at 650 nm), the visible part of the MEF spectrum almost perfectly matches the surface scattering signature.

It is shown herein that Au-clusters of 8- and 25-atom sizes, formed within a protein (BSA), have broad absorption and fluorescence spectra, from the UV to NIR. Further, in the presence of close-proximity surface deposited silver nanoparticles, the fluorescence signature of the Au-NCs is enhanced dramatically (maximal MEF is >50), but in a wavelength-dependent way, i.e. observed MEF is a function of the wavelength of fluorescence registration and excitation. MEF changes from 2-4 to 50 fold, depending on wavelength. It is shown that the MEF spectra closely matches the synchronous scattering spectra. This result is in agreement with the unified theory of Metal-Enhanced Fluorescence (25), which explains MEF as the near-field coupling of electronic excited states to induced surface plasmons of nanoparticles that, subsequently, radiate the photophysical characteristics of the coupled quanta.

Figure 31:
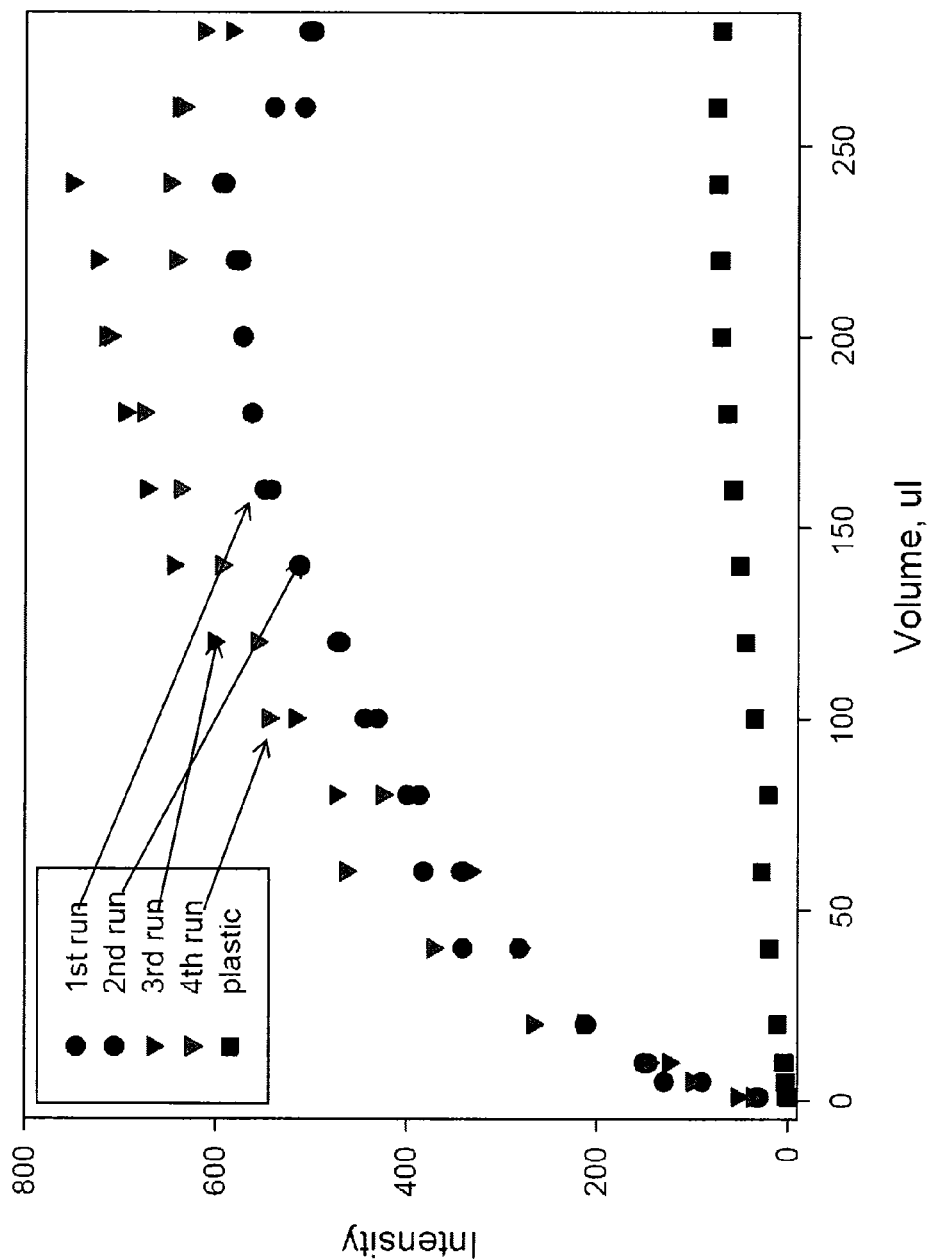
FIG. 31 shows the intensity of emissions of a conical shaped well coated with the multilayers of nanoparticles of the present invention.

The multilayers of discrete sized nanoparticles can be used to deposit on the surface of conical shaped assays wells. Conical shaped well are "V" shaped wells often used for low volume applications such as with DNA or PCR. It has been found that applying multiple layers of discrete nanoparticles of substantially the same size (that being same diameter) that there are enhancements of MEF up to about 100 fold. FIG. 31 shows the intensity of emissions from conical plates whereon 20 layers have been deposited wherein each deposition period was about four (4) minutes.

The multilayers of nanoparticles of the present invention enhance fluorescence, alpha-fluorescence, e-type fluorescence, p-type fluorescence, phosphorescence, chemiluminescence and emission which results from electron-hole recombination, i.e. quantum dots and carbon nanodots. The potential applications include the following:

As a substrate for luminescence assays (Fluorescence, chemiluminescence, long lived or off-gated phosphorescence). Assays including DNA, RNA and protein assays. In 96, 386 or 1536 HTS well plates.

In flow chambers for flow cytometry and cell counting.

In microfluidics for enhanced fluorescence detection.

As a coating (full coating or speckled) on beads or carbon nanodots.

As a shell (full coating or speckled) around quantum dots or luminescent beads.

As a substrate for Single Molecule detection or in Fluorescence Correlation Spectroscopy and their subsequent specialized wells.

In conjunction with the Microwave-Accelerated metal-enhanced Fluorescence technique for ultra-fast and sensitive assays.

In clothing, as a very bright luminescent enhancing substrate.

In safety wear or gear, where brightness is important for standing out.

As a coating for regions of paper and paper products, such as bank notes, bond certificates.

As a coating to generate singlet oxygen or super oxide anion radical for the disinfection of surfaces and the killing of bugs and bacteria.

To be used in conjunction with HRP-luminol chemiluminescence assays.

To be used on high density protein chips for the detection of small volumes of material.

To be used to detect proteins and protein fragments after labelling.

To be used in conjunction with PCR and qRT-PCR, to enhance the signatures of labels which have been thermally and cyclically amplified.

As a substrate to release the fluorescence of quenched entities, such as the release of over labelled protein fluorescence.

REFERENCES

The contents of the following references are incorporated by reference herein for all purposes 1. C. D. Geddes and J. R. Lakowicz, Journal of Fluorescence 12, 121-129 (2002).
2. K. Aslan, I. Gryczynski, J. Malicka, E. Matveeva, J. R. Lakowicz, and C. D. Geddes, Current Opinion in Biotechnology 16, 55-62 (2005).
3. K. Aslan, M. J. R. Previte, Y. X. Zhang, and C. D. Geddes, Biophysical Journal, 371A-371A (2007).
4. J. R. Lakowicz, Analytical Biochemistry 298, 1-24 (2001).
5. Y. Zhang, K. Aslan, M. J. Previte, and C. D. Geddes, Chemical Physics Letters 432, 528-532 (2006).
6. M. H. Chowdhury, K. Aslan, S. N. Malyn, J. R. Lakowicz, and C. D. Geddes, Applied Physics Letters 88, 173104 (2006).
7. Y. Zhang, K. Aslan, M. J. Previte, and C. D. Geddes, Applied Physics Letters 90, 053107 (2007).
8. K. Aslan, Z. Leonenko, J. R. Lakowicz, and C. D. Geddes, Journal of Fluorescence 15, 643-654 (2005).
9. J. Yguerabide and E. E. Yguerabide, Analytical Biochemistry 262, 137-156 (1998).
10. K. Aslan, S. N. Malyn, and C. D. Geddes, Analyst 132, 1112-1121 (2007).
11. K. Aslan, P. Holley, L. Davies, J. R. Lakowicz, and C. D. Geddes, Journal of the American Chemical Society 127, 12115-12121 (2005).
12. Y. Zhang, K. Aslan, M. J. R. Previte, and C. D. Geddes; Vol. 90 (AIP, 2007), p. 173116.
13. M. H. Chowdhury, S. N. Malyn, K. Aslan, J. R. Lakowicz, and C. D. Geddes, Journal of Physical Chemistry B 110, 22644-22651 (2006).
14. M. J. R. Previte, K. Aslan, Y. X. Zhang, and C. D. Geddes, Journal of Physical Chemistry C 111, 6051-6059 (2007).
15. C. Zhang, K. Abdijalilov, and H. Grebel, J Chem Phys 127, 044701 (2007).
16. K. R. Strehle, D. Cialla, P. Rosch, T. Henkel, M. Kohler, and J. Popp, Anal Chem 79, 1542-7 (2007).
17. Q. Yu and G. Golden, Langmuir 23, 8659-62 (2007).
18. K. Aslan, J. Huang, G. M. Wilson, and C. D. Geddes, Journal of the American Chemical Society 128, 4206-4207 (2006).
19. D. S. dos Santos and R. F. Aroca, Analyst 132, 450-454 (2007).
20. C. D. Geddes, A. Parfenov, D. Roll, J. Y. Fang, and J. R. Lakowicz, Langmuir 19, 6236-6241 (2003).
21. A. Feofanov, A. Ianoul, E. Kryukov, S. Maskevich, G. Vasiliuk, L. Kivach, and I. Nabiev, Analytical Chemistry 69, 3731-3740 (1997).
22. K. Aslan, P. Holley, and C. D. Geddes, Journal of Materials Chemistry 16, 2846-2852 (2006).
23. A. Retnakumari, S. Setua, D. Menon, P. Ravindran, H. Muhammed, T. Pradeep, S. Nair, and M. Koyakutty, Nanotechnology. 21 (2010) 055103.
24. C. I. Richards, S. Choi, J. C. Hsiang, Y. Antoku, T. Vosch, A. Bongiorno, Y. L. Tzeng, and R. M. Dickson, J. Am. Chem. Soc. 130 (2008) 5038.
25. K. Aslan and C. D. Geddes, (2010) Metal-enhanced fluorescence: progress towards a unified plasmon-fluorophore description., in: C. D. Geddes (Ed.) Metal-enhanced fluorescence., John Wiley & Sons, Inc., Hoboken, N.J., 2010 pp. 1-24.

That which is claimed is:

1. A method of fabricating a metallized substrate that includes multiple layers of metallic nanoparticles that exhibit increased metal enhanced fluorescence, the method comprising:
   a) providing a substrate;
   b) providing a metal containing solution, wherein the metal has plasmonic activity, contacting the metal containing solution with the substrate and heating same to a temperature of from about 30° C. to about 60° C. for a deposition time period ranging from 1 minute to 7 minutes to provide for deposition of metallic nanoparticles;
   c) transferring the heated substrate to a freezing chamber for a time period ranging from about 1 minute to 4 minutes to form a chilled substrate;
   d) transferring the chilled substrate back to a heating environment for a time period as in step b) or shorter than the previous heating period and in the same heating temperature range;
   e) removing the solution; and
   f) repeating steps b) and c) for at least one more time and optionally from 4 to 19 times to provide a multiplicity of layers of metallic nanoparticles, wherein the nanoparticles are discrete and substantially the same size.

2. The method according to claim 1, wherein the metal containing solution comprises $AgNO_3$ with a concentration of about 1% to about 5% w/v.

3. The method of claim 2, wherein the metal containing solution further comprising NaOH having a concentration of about 5% to about 20% w/v in an amount from about 50 ul to about 100 ul, $NH_4OH$ having a concentration of about 20% to 40% w/v in an amount from about 300 ul to about 700 ul and glucose in an amount from about 2 ml to about 7 ml to provide from about 5 to 15% w/v of glucose.

4. The method of claim 1, wherein the metal containing solution comprises a metal selected from the group consisting of Silver, Gold, Aluminium, Zinc, Rhodium, Copper, Nickel, Palladium, Indium, Tin, Iron, Tungsten, Platinum, Germanium and a combination thereof.

5. The method of claim 1, wherein the substrate is fabricated from glass, quartz, metallic oxide or a polymeric material.

6. The method of claim 1, wherein the metallic nanoparticles have an approximate cross-sectional diameter from about 100 nm to about 350 nm.

7. The method of claim 1, wherein the heating deposition time is from about 4 to 7 minutes.

8. The method of claim 1, wherein the discrete layers of metallic nanoparticles is from 2 to 12 layers.

9. The method of claim 1, wherein the metal containing solution comprises 200 µl of sodium hydroxide solution (0.5% w/v), 60 ml of $AgNO_3$ (0.83% w/v), 2 ml of ammonium hydroxide (30% w/v solution) and 15 ml of fresh D-glucose solution (4.8% w/v).

10. The method of claim 7, wherein the heating deposition time is repeated 7 to 12 times to provide 7 to 12 discrete layers.

11. The method of claim 1, wherein the substrate is a High Throughput Screening (HTS) plate.

12. The method of claim 1, wherein the substrate is plasma treated to provide a hydrophilic surface.

13. The method of claim 1, wherein the substrate is a substantially flat surface.

14. A detection method exhibiting increased fluorescence emitted from the system during metal-enhanced fluorescence sensing, the detection method comprising:
   i) providing a metallized surface container with a multiplicities of layers of metallic nanoparticles, the metallized surface container fabricated by the following method,
   a) providing a plasma cleaned substrate type container having at least a bottom point and sides attached to the bottom point;
   b) providing a silver containing solution and pouring into the plasma cleaned substrate container and heating same to a temperature of from about 30° C. to about 50° C. for a time period ranging from 1 minute to 4 minutes to form a heated substrate;
   c) transferring the heated substrate to a freezing chamber for a time period range from about 1 minute to 4 minutes to form a cold substrate;
   d) transferring the cold substrate back to a heating environment for a time being the same as step b) or shorter than the previous heating period;
   e) removing the solution; and
   f) repeating steps b) and c) from at least one more time, and optionally from about 4 to 19 times to provide a multiplicity of layers of silver nanoparticles, wherein the nanoparticles are distinct and substantially the same size;
   ii) providing an intrinsic or extrinsic fluorophore for disposing near the near the surface of the top layer of nanoparticles;
   iii) exciting the fluorophore with an electromagnetic source to cause fluorescing; and
   iv) measuring the emissions from the system.

15. The method of claim 14, wherein the intrinsic or extrinsic fluorophore is positioned from about 5 nm to about 30 nm from the top layer of metallic nanoparticles.

16. The method of claim 14, wherein the emissions are in wavelengths from UV-visible to near IR.

17. The method of claim 14, wherein the extrinsic fluorophore is attached to a biomolecule.

18. The method of claim 14, wherein the metallic nanoparticles positioned on the top surface of the multiple layers have attached thereto receptor molecules having affinity for a ligand of interest suspected of being in a testing sample.

* * * * *